United States Patent
Bodhuri et al.

(10) Patent No.: US 9,260,438 B2
(45) Date of Patent: Feb. 16, 2016

(54) SOLID FORMS OF TOFACITINIB SALTS

(71) Applicant: APOTEX INC., Toronto (CA)

(72) Inventors: Prabhudas Bodhuri, Brantford (CA);
Stuart P. Green, Mount Pleasant (CA);
Fan Wang, Burlington (CA); Cameron L. McPhail, Brantford (CA); Eduardo Gustavo Cammisa, Markham (CA);
Avedis Karadeolian, Cambridge (CA)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 14/616,001

(22) Filed: Feb. 6, 2015

(65) Prior Publication Data

US 2015/0225406 A1     Aug. 13, 2015

Related U.S. Application Data

(60) Provisional application No. 61/936,833, filed on Feb. 6, 2014, provisional application No. 61/977,607, filed on Apr. 9, 2014.

(51) Int. Cl.
  *C07C 51/41*     (2006.01)
  *C07D 487/04*     (2006.01)

(52) U.S. Cl.
  CPC ............. *C07D 487/04* (2013.01); *C07C 51/41* (2013.01); *C07B 2200/13* (2013.01)

(58) Field of Classification Search
  CPC ....................................................... C07C 51/41
  See application file for complete search history.

(56) References Cited

FOREIGN PATENT DOCUMENTS

| | | | |
|---|---|---|---|
| CN | 103073552 A | 5/2013 | |
| WO | 0142246 A2 | 6/2001 | |
| WO | 02096909 A1 | 12/2002 | |
| WO | 03048162 A1 | 6/2003 | |
| WO | WO 03/048162 * | 6/2003 | ........... C07D 487/04 |
| WO | 2012135338 A1 | 10/2012 | |
| WO | 2012137111 A1 | 10/2012 | |
| WO | 2013090490 A1 | 6/2013 | |

* cited by examiner

*Primary Examiner* — Erich A Leeser
(74) *Attorney, Agent, or Firm* — The Webb Law Firm

(57) ABSTRACT

Solid and crystalline forms of tofacitinib hydrochloride and tofacitinib hydrobromide, processes for the preparation thereof and processes for the use thereof in preparing tofacitinib citrate are provided.

4 Claims, 18 Drawing Sheets

SOLID FORMS OF TOFACITINIB SALTS

CROSS-REFERENCES TO RELATED APPLICATIONS

The present application claims the benefit of U.S. Provisional Application No. 61/936,833, filed on Feb. 6, 2014, entitled "SOLID FORMS OF TOFACITINIB HYDROCHLORIDE", which is hereby incorporated by reference in its entirety for all purposes. The present application also claims the benefit of U.S. Provisional Application 61/977,607, filed on Apr. 9, 2014, entitled "SOLID FORMS OF TOFACITINIB SALTS" which is hereby incorporated by reference in its entirety for all purposes.

TECHNICAL FIELD

The present invention relates to solid forms of salts of tofacitinib.

BACKGROUND

3-[(3R,4R)-4-Methyl-3-[methyl-(7H-pyrrolo[2,3-d]pyrimidin-4-yl)-amino]piperidin-1-yl]-3-oxopropionitrile (Formula 1), commonly known as tofacitinib, is disclosed in WO 01/42246 A1 and WO 02/096909 A1. XELJANZ™ a commercial form of the citrate salt of tofacitinib, is indicated for the treatment of adult patients with moderately to severely active rheumatoid arthritis who have had an inadequate response or intolerance to methotrexate.

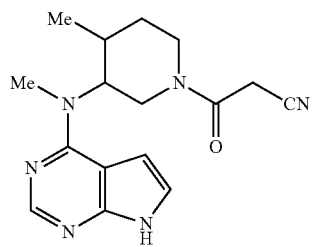

(1)

WO 03/048162 A1 relates to a novel amorphous and crystalline forms of 3-{(3R,4R)-4-methyl-3-[methyl-(7H-pyrrolo[2,3-d]pyrimidin-4-yl)-amino]-piperidin-1-yl}-3-oxopropionitrile mono-citrate salt, useful as inhibitors of protein kinases, and to their methods of preparation.

WO 2012/135338 A1 is directed to tofacitinib acid addition salts and solid state forms thereof, particularly amorphous tofacitinib acetate, as well as pharmaceutical compositions comprising one or more of them. The invention further provides a process for producing tofacitinib acid addition salt, in particular, tofacitinib mono-citrate salt.

WO 2012/137111 A1 discloses novel crystalline and non-crystalline forms of 3-((3R,4R)-4-methyl-3-[methyl-(7H-pyrrolo[2,3-d]pyrimidin-4-yl)-amino]-piperidin-1-yl)-3-oxopropionitrile, pharmaceutical composition containing the same, preparations thereof and the uses thereof.

WO 2013/090490 A1 is directed to several tofacitinib salts including tofacitinib mono-tartrate salt, tofacitinib mono-malate salt and tofacitinib mono-oxalate salt. These tofacitinib salts can be in amorphous form. The invention is also directed toward a pharmaceutical composition comprising one or more of the tofacitinib salts, and a process for preparing the composition. The tofacitinib salts can be used to prepare tofacitinib mono-citrate salt. Another aspect of the invention is a process for preparing tofacitinib mono-citrate. The tofacitinib salts of the invention are also useful as medicaments and in methods of treating patients suffering from cancer.

CN 103073552 A provides a preparation method for amorphous tofacitinib citrate. The preparation method is simple, can easily obtain high-purity amorphous tofacitinib citrate, and is suitable for industrial application. The preparation method includes the following steps: under the temperature range between 30° C. and 50° C., organic solvent is used for dissolving tofacitinib citrate, so that solution is produced, water which is 15° C. to 25° C. is added into the solution, so that precipitate is produced, the precipitate is put in the environment of 15° C. to 25° C. for 4 to 24 hours, and the amorphous tofacitinib citrate is then recovered.

SUMMARY

This invention is based, at least in part, on solid forms of tofacitinib hydrochloride and tofacitinib hydrobromide. Solid forms of tofacitinib hydrochloride and tofacitinib hydrobromide disclosed herein may have higher water solubility compared to a crystalline form of tofacitinib citrate.

In Illustrative embodiments, there is provided, a crystalline form of tofacitinib hydrochloride.

In Illustrative embodiments, there is provided, a crystalline form described herein characterized by a PXRD comprising peaks, expressed in degrees 2-theta, at approximately 5.7±0.2, 13.8±0.2, 15.9±0.2, 17.2±0.2, 18.9±0.2 and 21.0±0.2.

In Illustrative embodiments, there is provided, a crystalline form described herein characterized by a PXRD substantially similar to the PXRD as depicted in FIG. 1.

In Illustrative embodiments, there is provided, a crystalline form described herein characterized by a PXRD substantially similar to the PXRD as depicted in FIG. 3.

In Illustrative embodiments, there is provided, a crystalline form described herein comprising acetone wherein the weight percentage of acetone is from about 3.9 wt % to about 16.6 wt %.

In Illustrative embodiments, there is provided, a crystalline form described herein comprising acetone wherein the weight percentage of acetone to tofacitinib hydrochloride is from about 9.4 to about 14.0 wt %.

In Illustrative embodiments, there is provided, a crystalline form described herein characterized by a PXRD comprising peaks, expressed in degrees 2-theta, at approximately 5.6±0.2, 13.8±0.2, 16.0±0.2, 16.7±0.2, 17.7±0.2 and 21.0±0.2.

In Illustrative embodiments, there is provided, a crystalline form described herein comprising N,N-dimethylformamide wherein the weight percentage of N,N-dimethylformamide is from about 11.2 wt % to about 17.3 wt %.

In Illustrative embodiments, there is provided, a crystalline form described herein characterized by a PXRD substantially similar to the PXRD as depicted in FIG. 4.

In Illustrative embodiments, there is provided, a crystalline form described herein characterized by a PXRD comprising peaks, expressed in degrees 2-theta, at approximately 5.7±0.2, 11.4±0.2, 13.8±0.2, 14.4±0.2, 19.8±0.2, 21.6±0.2 and 22.8±0.2.

In Illustrative embodiments, there is provided, a crystalline form described herein comprising dimethyl sulfoxide wherein the weight percentage of dimethyl sulfoxide is from about 15.2 wt % to about 21.2 wt %.

In Illustrative embodiments, there is provided, a crystalline form described herein characterized by a PXRD substantially similar to the PXRD as depicted in FIG. 5.

In Illustrative embodiments, there is provided, a crystalline form described herein characterized by a PXRD comprising peaks, expressed in degrees 2-theta, at approximately 6.6±0.2, 11.8±0.2, 17.4±0.2, 21.3±0.2, 25.3±0.2 and 26.2±0.2.

In Illustrative embodiments, there is provided, a crystalline form described herein characterized by a PXRD substantially similar to the PXRD as depicted in FIG. 6.

In Illustrative embodiments, there is provided, a crystalline form described herein characterized by a PXRD comprising peaks, expressed in degrees 2-theta, at approximately 5.6±0.2, 11.4±0.2, 16.3±0.2, 21.7±0.2, 23.5±0.2 and 28.2±0.2.

In Illustrative embodiments, there is provided, a crystalline form described herein comprising N,N-dimethylacetamide wherein the weight percentage of N,N-dimethylacetamide is from about 14.9 wt % to about 21.5 wt %.

In Illustrative embodiments, there is provided, a crystalline form described herein characterized by a PXRD substantially similar to the PXRD as depicted in FIG. 8.

In Illustrative embodiments, there is provided, a crystalline form described herein characterized by a PXRD comprising peaks, expressed in degrees 2-theta, at approximately 6.9±0.2, 13.2±0.2, 17.9±0.2, 18.9±0.2, 20.2±0.2 and 24.1±0.2.

In Illustrative embodiments, there is provided, a crystalline form described herein characterized by a PXRD substantially similar to the PXRD as depicted in FIG. 9.

In Illustrative embodiments, there is provided, a crystalline form described herein characterized by a PXRD comprising peaks, expressed in degrees 2-theta, at approximately 6.1±0.2, 11.5±0.2, 13.0±0.2, 16.7±0.2, 18.8±0.2 and 20.8±0.2.

In Illustrative embodiments, there is provided, a crystalline form described herein comprising methyl ethyl ketone wherein the weight percentage of methyl ethyl ketone is from about 14.9 wt % to about 21.5 wt %.

In Illustrative embodiments, there is provided, a crystalline form described herein characterized by a PXRD substantially similar to the PXRD as depicted in FIG. 10.

In Illustrative embodiments, there is provided, a crystalline form described herein characterized by a PXRD comprising peaks, expressed in degrees 2-theta, at approximately 5.9±0.2, 6.6±0.2, 13.0±0.2, 14.0±0.2, 15.0±0.2 and 20.9±0.2.

In Illustrative embodiments, there is provided, a crystalline form described herein characterized by a PXRD substantially similar to the PXRD as depicted in FIG. 11.

In Illustrative embodiments, there is provided, a process for the preparation of a crystalline form of tofacitinib hydrochloride, the process comprising: a) combining hydrogen chloride with tofacitinib free base and an organic solvent selected from the group consisting of $C_3$-$C_7$ ketones, N,N-dialkylamides, alkyl nitriles, alkyl sulfoxides and nitroalkanes thereby obtaining a precipitate; and b) isolating the precipitate to yield crystalline tofacitinib hydrochloride.

In Illustrative embodiments, there is provided, a process described herein wherein the hydrogen chloride is provided as a solution of hydrogen chloride in 1,4-dioxane or as a solution of hydrogen chloride in isopropanol or as an aqueous solution of hydrogen chloride.

In Illustrative embodiments, there is provided, a process for the preparation of a crystalline form of tofacitinib hydrochloride, the process comprising: a) suspending amorphous tofacitinib hydrochloride in an organic solvent selected from the group consisting of $C_3$-$C_7$ ketones, N,N-dialkylamides, alkyl nitriles, alkyl sulfoxides and nitroalkanes thereby obtaining a precipitate; and b) isolating the precipitate to yield crystalline tofacitinib hydrochloride.

In Illustrative embodiments, there is provided, a process described herein wherein the organic solvent is selected from the group consisting of acetone, methyl ethyl ketone, N,N-dimethylformamide, N,N-dimethylacetamide, acetonitrile, dimethyl sulfoxide and nitromethane.

In Illustrative embodiments, there is provided, a process for the preparation of tofacitinib citrate, the process comprising combining tofacitinib hydrochloride with a source of citrate ion.

In Illustrative embodiments, there is provided, a process described herein wherein the source of citrate ion is citric acid or a dihydrogen citrate salt.

In Illustrative embodiments, there is provided, a process described herein wherein the dihydrogen citrate salt is an alkali metal dihydrogen citrate salt.

In Illustrative embodiments, there is provided, a process described herein wherein the dihydrogen citrate salt is monosodium citrate.

In Illustrative embodiments, there is provided, a process described herein wherein the dihydrogen citrate salt is prepared in situ by reacting citric acid with a base in the presence of tofacitinib hydrochloride.

In Illustrative embodiments, there is provided, a process described herein wherein the base is selected from the group consisting of metal hydroxides, metal carbonates, metal bicarbonates and amines.

In Illustrative embodiments, there is provided, a crystalline form of tofacitinib hydrobromide.

In Illustrative embodiments, there is provided, a crystalline form described herein characterized by a PXRD comprising peaks, expressed in degrees 2-theta, at approximately 6.1±0.2, 12.6±0.2, 19.1±0.2, 21.0±0.2, 23.9±0.2 and 25.4±0.2.

In Illustrative embodiments, there is provided, a crystalline form described herein comprising acetonitrile wherein the weight percentage of acetonitrile is from about 4.1 wt % to about 6.0 wt %.

In Illustrative embodiments, there is provided, a crystalline form described herein characterized by a PXRD substantially similar to the PXRD as depicted in FIG. 13.

In Illustrative embodiments, there is provided, a crystalline form described herein characterized by a PXRD comprising peaks, expressed in degrees 2-theta, at approximately 6.1±0.2, 12.0±0.2, 13.6±0.2, 19.7±0.2, 20.8±0.2 and 25.5±0.2.

In Illustrative embodiments, there is provided, a crystalline form described herein comprising acetone wherein the weight percentage of acetone is from about 4.8 wt % to about 7.1 wt %.

In Illustrative embodiments, there is provided, a crystalline form described herein characterized by a PXRD substantially similar to the PXRD as depicted in FIG. 14.

In Illustrative embodiments, there is provided, a crystalline form described herein characterized by a PXRD comprising peaks, expressed in degrees 2-theta, at approximately 5.6±0.2, 16.8±0.2, 21.2±0.2, 22.3±0.2, 24.0±0.2 and 24.7±0.2.

In Illustrative embodiments, there is provided, a crystalline form described herein comprising N,N-dimethylformamide wherein the weight percentage of N,N-dimethylformamide is from about 10.4 wt % to about 14.8 wt %.

In Illustrative embodiments, there is provided, a crystalline form described herein characterized by a PXRD substantially similar to the PXRD as depicted in FIG. 15.

In Illustrative embodiments, there is provided, a crystalline form described herein characterized by a PXRD comprising peaks, expressed in degrees 2-theta, at approximately 5.6±0.2, 16.2±0.2, 17.7±0.2, 21.6±0.2, 23.5±0.2 and 25.1±0.2.

In Illustrative embodiments, there is provided, a crystalline form described herein comprising N,N-dimethylacetamide wherein the weight percentage of N,N-dimethylacetamide is from about 12.5 wt % to about 17.7 wt %.

In Illustrative embodiments, there is provided, a crystalline form described herein characterized by a PXRD substantially similar to the PXRD as depicted in FIG. 16.

In Illustrative embodiments, there is provided, a crystalline form described herein characterized by a PXRD comprising peaks, expressed in degrees 2-theta, at approximately 5.7±0.2, 6.9±0.2, 13.1±0.2, 17.8±0.2, 24.0±0.2 and 24.9±0.2.

In Illustrative embodiments, there is provided, a crystalline form described herein comprising acetone wherein the weight percentage of acetone is from about 4.4 wt % to about 6.5 wt %.

In Illustrative embodiments, there is provided, a crystalline form described herein characterized by a PXRD substantially similar to the PXRD as depicted in FIG. 17.

In Illustrative embodiments, there is provided, a crystalline form described herein characterized by a PXRD comprising peaks, expressed in degrees 2-theta, at approximately 5.7±0.2, 13.7±0.2, 14.3±0.2, 20.8±0.2, 21.4±0.2 and 27.5±0.2.

In Illustrative embodiments, there is provided, a crystalline form described herein comprising acetone wherein the weight percentage of acetone is from about 7.6 wt % to about 11.0 wt %.

In Illustrative embodiments, there is provided, a crystalline form described herein characterized by a PXRD substantially similar to the PXRD as depicted in FIG. 18.

In Illustrative embodiments, there is provided, a process for the preparation of a crystalline form of tofacitinib hydrobromide, the process comprising: a) suspending amorphous tofacitinib hydrobromide in an organic solvent selected from the group consisting of acetone, alkyl nitriles and mixtures of N,N-dialkylamides with alkyl esters thereby obtaining a precipitate; and b) isolating the precipitate to yield crystalline tofacitinib hydrobromide.

In Illustrative embodiments, there is provided, a process described herein wherein the organic solvent is selected from the group consisting of acetone, acetonitrile, a mixture of N,N-dimethylformamide with ethyl acetate and a mixture of N,N-dimethylacetamide with ethyl acetate.

In Illustrative embodiments, there is provided, a process for the preparation of a crystalline form of tofacitinib hydrobromide, the process comprising: a) combining hydrogen bromide with tofacitinib free base and an organic solvent selected from the group consisting of acetone, alkyl nitriles and mixtures of N,N-dialkylamides with alkyl esters thereby obtaining a precipitate; and b) isolating the precipitate to yield crystalline tofacitinib hydrobromide.

In Illustrative embodiments, there is provided, a process described herein wherein the hydrogen bromide is provided as a solution of hydrogen bromide in 1,4-dioxane or as a solution of hydrogen bromide in isopropanol or as an aqueous solution of hydrogen bromide.

In Illustrative embodiments, there is provided, a process for the preparation of tofacitinib citrate, the process comprising combining tofacitinib hydrobromide with a source of citrate ion.

In Illustrative embodiments, there is provided, a process described herein wherein the source of citrate ion is citric acid or a dihydrogen citrate salt.

In Illustrative embodiments, there is provided, a process described herein wherein the dihydrogen citrate salt is an alkali metal dihydrogen citrate salt.

In Illustrative embodiments, there is provided, a process described herein wherein the dihydrogen citrate salt is monosodium citrate.

In Illustrative embodiments, there is provided, a process described herein wherein the dihydrogen citrate salt is prepared in situ by reacting citric acid with a base in the presence of tofacitinib hydrobromide.

In Illustrative embodiments, there is provided, a process described herein wherein the base is selected from the group consisting of metal hydroxides, metal carbonates, metal bicarbonates and organic amines.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

When used in reference to a diffractogram, a spectrum and/or data presented in a graph, the term "substantially similar" means that the subject diffractogram, spectrum and/or data presented in a graph encompasses all diffractograms, spectra and/or data presented in graphs that vary within acceptable boundaries of experimentation that are known to a person of skill in the art. Such boundaries of experimentation will vary depending on the type of the subject diffractogram, spectrum and/or data presented in a graph, but will nevertheless be known to a person of skill in the art.

When used in reference to a peak in a PXRD diffractogram, the term "approximately" means that the peak may vary by ±0.2 degrees 2-theta of the subject value.

As used herein, when referring to a diffractogram, spectrum and/or to data presented in a graph, the term "peak" refers to a feature that one skilled in the art would recognize as not attributing to background noise.

Depending on the nature of the methodology applied and the scale selected to display results obtained from an X-ray diffraction analysis, an intensity of a peak obtained may vary quite dramatically. For example, it is possible to obtain a relative peak intensity of 1% when analyzing one sample of a substance, but another sample of the same substance may show a much different relative intensity for a peak at the same position. This may be due, in part, to the preferred orientation of the sample and its deviation from the ideal random sample orientation, sample preparation and the methodology applied. Such variations are known and understood by a person of skill in the art.

The present invention encompasses the polymorphic forms isolated in pure form or when admixed with other materials, for example other isomers and/or polymorphic forms and/or salt forms or any other material.

As used herein, when referring to a solvent content, the term "weight percentage" (wt %) refers to the ratio: weight solvent/(weight solvent+weight tofacitinib hydrochloride), expressed as a percentage.

In one embodiment, the present invention comprises Form APO-A tofacitinib hydrochloride.

Figure 1:
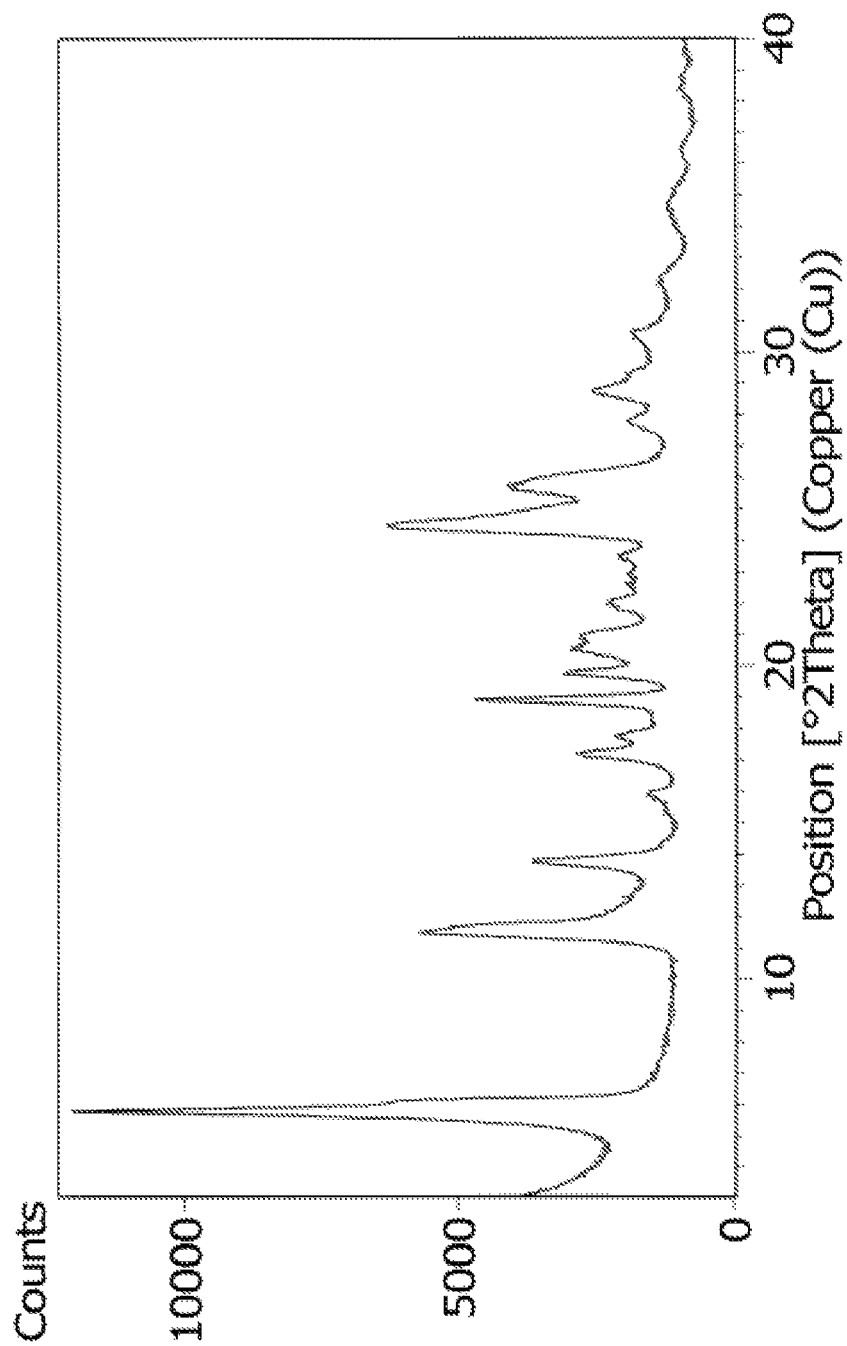
FIG. 1 is a Powder X-Ray Diffractogram (PXRD) of Form APO-A tofacitinib hydrochloride obtained according to Example 2 (damp cake).

An illustrative PXRD diffractogram of Form APO-A tofacitinib hydrochloride obtained according to the conditions given in Example 2 (damp cake) is shown in FIG. 1. According to FIG. 1, the Form APO-A tofacitinib hydrochloride may have a reflection ("peak") at any one or more of the values expressed in degrees 2-theta given in Table 1. Although values are given in the tables below, the form may be defined by the claimed peaks. Further, a particular claim may be limited to one peak only, or several peaks. The Form APO-A tofacitinib hydrochloride does not have to include all or even many of the peaks listed in Table 1. Some illustrative and non-limiting possible observations regarding relative intensities of the peaks are set out in Table 1.

TABLE 1

Form APO-A tofacitinib hydrochloride obtained from Example 2 (damp cake)

| Peak (degrees 2-theta) | Relative Intensity (%) |
|---|---|
| 5.75 | 100.00 |
| 11.44 | 35.75 |
| 11.69 | 24.08 |
| 13.77 | 21.85 |
| 15.90 | 5.21 |
| 17.15 | 15.17 |
| 17.72 | 8.45 |
| 18.89 | 34.60 |
| 19.75 | 17.59 |
| 20.51 | 15.96 |
| 20.99 | 11.32 |
| 21.97 | 10.63 |
| 23.48 | 4.46 |
| 24.43 | 45.24 |
| 25.76 | 24.83 |
| 26.18 | 6.69 |
| 27.71 | 6.12 |
| 28.73 | 12.25 |

In an embodiment, Form APO-A may be characterized by a PXRD comprising peaks, expressed in degrees 2-theta, at approximately 5.7±0.2, 13.8±0.2, 15.9±0.2, 17.2±0.2, 18.9±0.2 and 21.0±0.2.

In an embodiment, Form APO-A tofacitinib hydrochloride comprises from about 3.9 wt % to about 16.6 wt % acetone.

Figure 2:
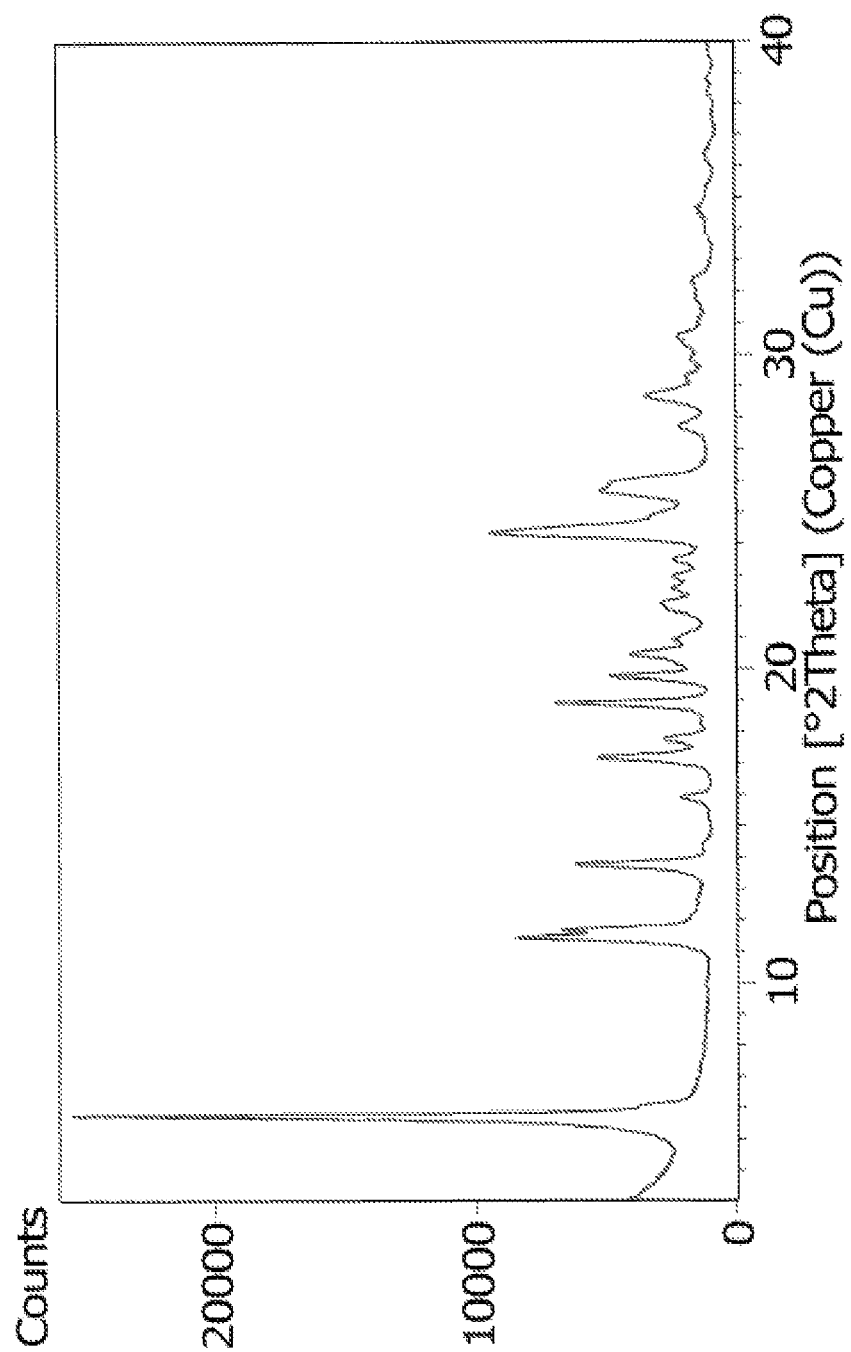
FIG. 2 is a Powder X-Ray Diffractogram (PXRD) of Form APO-A tofacitinib hydrochloride obtained according to Example 2 (dried product).

An illustrative PXRD diffractogram of Form APO-A tofacitinib hydrochloride obtained according to the conditions given in Example 2 (dried product) is shown in FIG. 2. According to FIG. 2, the Form APO-A tofacitinib hydrochloride may have a reflection ("peak") at any one or more of the values expressed in degrees 2-theta given in Table 2. Although values are given in the tables below, the form may be defined by the claimed peaks. Further, a particular claim may be limited to one peak only, or several peaks. The Form APO-A tofacitinib hydrochloride does not have to include all or even many of the peaks listed in Table 2. Some illustrative and non-limiting possible observations regarding relative intensities of the peaks are set out in Table 2.

TABLE 2

Form APO-A tofacitinib hydrochloride obtained from Example 2 (damp cake)

| Peak (degrees 2-theta) | Relative Intensity (%) |
|---|---|
| 5.73 | 100.00 |
| 11.42 | 36.59 |
| 11.68 | 25.83 |
| 13.78 | 22.15 |
| 15.89 | 6.04 |
| 17.16 | 23.37 |
| 17.74 | 9.59 |
| 18.92 | 28.04 |
| 19.74 | 19.99 |
| 20.45 | 16.56 |
| 20.98 | 4.83 |
| 21.92 | 8.76 |
| 22.53 | 6.58 |
| 22.93 | 6.86 |

TABLE 2-continued

Form APO-A tofacitinib hydrochloride
obtained from Example 2 (damp cake)

| Peak (degrees 2-theta) | Relative Intensity (%) |
| --- | --- |
| 23.46 | 6.59 |
| 24.33 | 45.21 |
| 25.63 | 20.44 |
| 25.96 | 14.89 |
| 27.72 | 6.29 |
| 28.67 | 13.87 |

Figure 3:
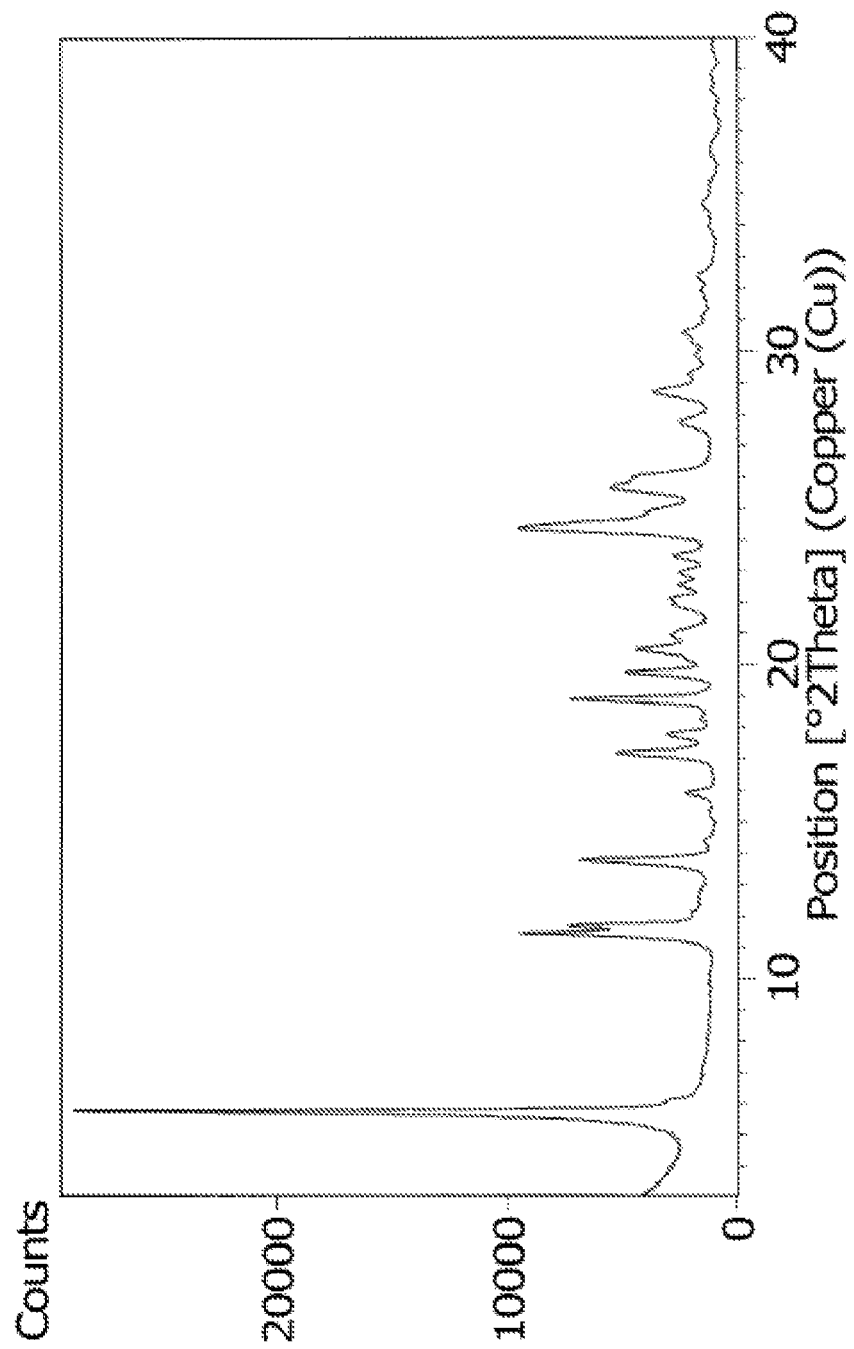
FIG. 3 is a Powder X-Ray Diffractogram (PXRD) of Form APO-A tofacitinib hydrochloride obtained according to Example 3.

An illustrative PXRD diffractogram of Form APO-A tofacitinib hydrochloride obtained according to the conditions given in Example 3 is shown in FIG. 3. According to FIG. 3, the Form APO-A tofacitinib hydrochloride may have a reflection ("peak") at any one or more of the values expressed in degrees 2-theta given in Table 3. Although values are given in the tables below, the form may be defined by the claimed peaks. Further, a particular claim may be limited to one peak only, or several peaks. The Form APO-A tofacitinib hydrochloride does not have to include all or even many of the peaks listed in Table 3. Some illustrative and non-limiting possible observations regarding relative intensities of the peaks are set out in Table 3.

TABLE 3

Form APO-A tofacitinib hydrochloride obtained from Example 3

| Peak (degrees 2-theta) | Relative Intensity (%) |
| --- | --- |
| 5.73 | 100.00 |
| 11.43 | 37.95 |
| 11.69 | 24.53 |
| 13.80 | 15.57 |
| 15.90 | 5.22 |
| 17.17 | 20.68 |
| 17.75 | 8.64 |
| 18.91 | 22.76 |
| 19.74 | 17.90 |
| 20.48 | 15.67 |
| 20.98 | 7.28 |
| 21.89 | 6.77 |
| 22.52 | 5.84 |
| 22.93 | 6.52 |
| 23.46 | 6.62 |
| 24.30 | 27.81 |
| 25.63 | 20.59 |
| 25.99 | 12.30 |
| 27.71 | 6.40 |
| 28.68 | 11.54 |

Figure 4:
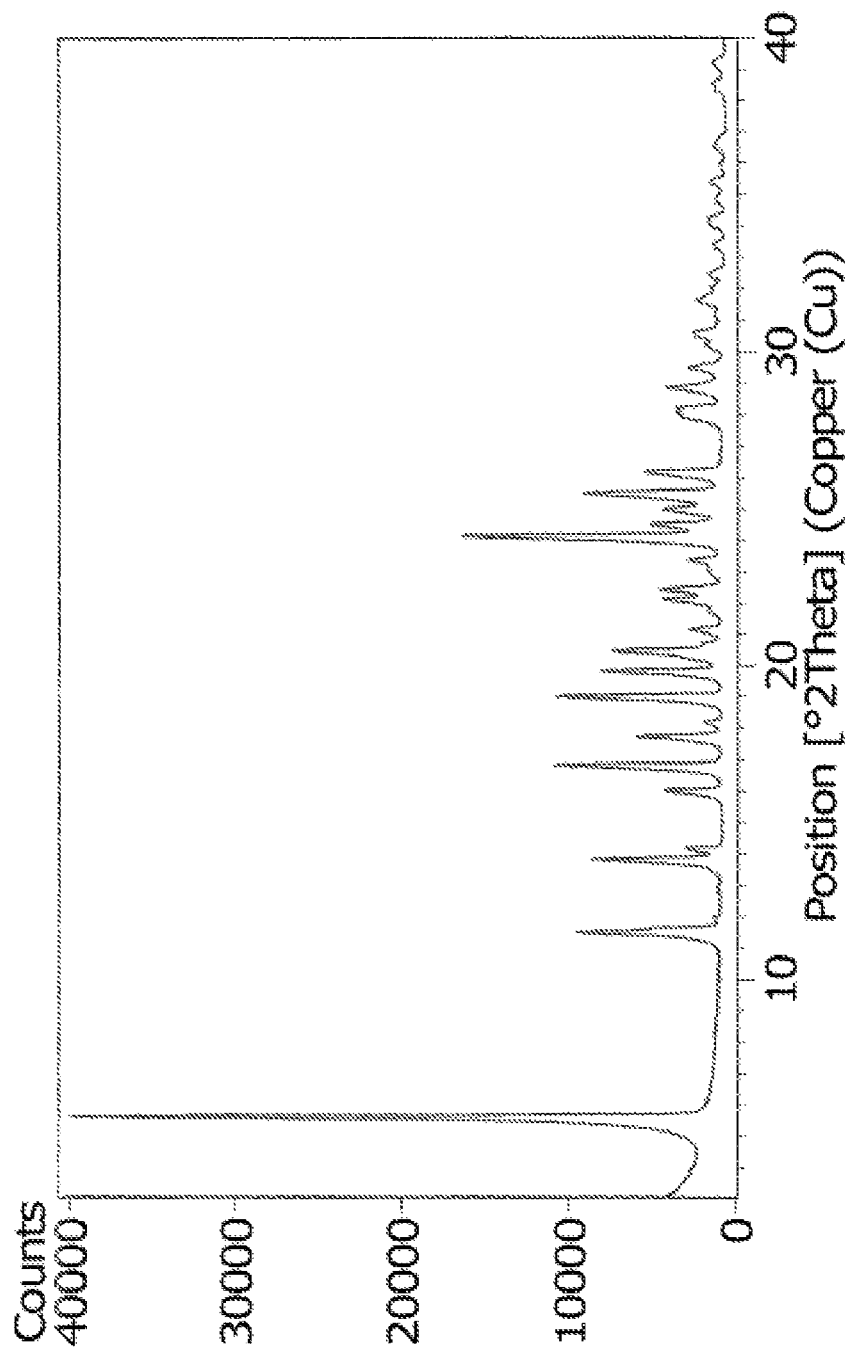
FIG. 4 is a Powder X-Ray Diffractogram (PXRD) of Form APO-B tofacitinib hydrochloride obtained according to Example 4.

An illustrative PXRD diffractogram of Form APO-B tofacitinib hydrochloride obtained according to the conditions given in Example 4 is shown in FIG. 4. According to FIG. 4, the Form APO-B tofacitinib hydrochloride may have a reflection ("peak") at any one or more of the values expressed in degrees 2-theta given in Table 4. Although values are given in the tables below, the form may be defined by the claimed peaks. Further, a particular claim may be limited to one peak only, or several peaks. The Form APO-B tofacitinib hydrochloride does not have to include all or even many of the peaks listed in Table 4. Some illustrative and non-limiting possible observations regarding relative intensities of the peaks are set out in Table 4.

TABLE 4

Form APO-B tofacitinib hydrochloride obtained from Example 4

| Peak (degrees 2-theta) | Relative Intensity (%) |
| --- | --- |
| 5.61 | 100.00 |
| 11.48 | 25.46 |
| 11.64 | 8.42 |
| 13.81 | 24.46 |
| 14.17 | 6.59 |
| 15.99 | 10.94 |
| 16.72 | 14.79 |
| 17.71 | 16.72 |
| 18.19 | 4.42 |
| 19.01 | 29.41 |
| 20.45 | 21.98 |
| 21.13 | 6.21 |
| 22.09 | 11.07 |
| 22.41 | 12.02 |
| 23.35 | 6.22 |
| 24.10 | 40.98 |
| 24.46 | 13.10 |
| 24.95 | 11.05 |
| 25.48 | 20.98 |
| 26.10 | 14.76 |
| 27.96 | 8.49 |
| 28.82 | 11.12 |
| 29.46 | 6.25 |
| 30.55 | 5.71 |

In an embodiment, Form APO-B tofacitinib hydrochloride may be characterized by a PXRD comprising peaks, expressed in degrees 2-theta, at approximately 5.6±0.2, 13.8±0.2, 16.0±0.2, 16.7±0.2, 17.7±0.2 and 21.0±0.2.

In an embodiment, Form APO-B tofacitinib hydrochloride comprises from about 11.2 wt % to about 17.3 wt % N,N-dimethylformamide.

Figure 5:
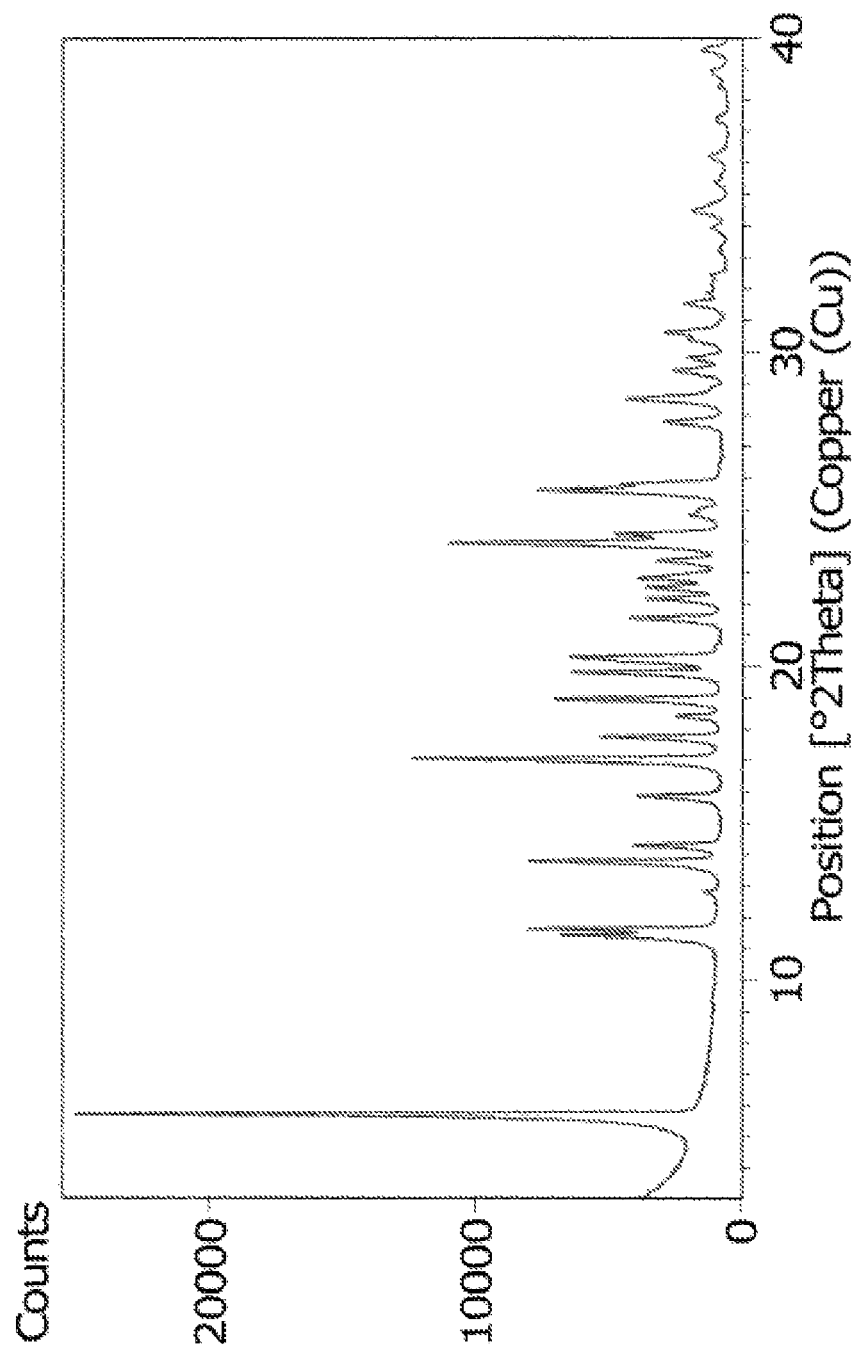
FIG. 5 is a Powder X-Ray Diffractogram (PXRD) of Form APO-C tofacitinib hydrochloride obtained according to Example 5.

An illustrative PXRD diffractogram of Form APO-C tofacitinib hydrochloride obtained according to the conditions given in Example 5 is shown in FIG. 5. According to FIG. 5, the Form APO-C tofacitinib hydrochloride may have a reflection ("peak") at any one or more of the values expressed in degrees 2-theta given in Table 5. Although values are given in the tables below, the form may be defined by the claimed peaks. Further, a particular claim may be limited to one peak only, or several peaks. The Form APO-C tofacitinib hydrochloride does not have to include all or even many of the peaks listed in Table 5. Some illustrative and non-limiting possible observations regarding relative intensities of the peaks are set out in Table 5.

TABLE 5

Form APO-C tofacitinib hydrochloride obtained from Example 5

| Peak (degrees 2-theta) | Relative Intensity (%) |
| --- | --- |
| 5.68 | 100.00 |
| 11.41 | 28.67 |
| 11.62 | 33.73 |
| 13.79 | 33.65 |
| 14.28 | 16.14 |
| 15.85 | 16.08 |
| 17.05 | 55.91 |
| 17.73 | 21.60 |
| 18.40 | 7.70 |
| 18.96 | 29.25 |
| 19.78 | 29.61 |
| 20.15 | 18.18 |
| 20.28 | 27.67 |
| 21.50 | 19.00 |
| 22.13 | 16.22 |
| 22.48 | 13.63 |
| 22.79 | 17.66 |

TABLE 5-continued

Form APO-C tofacitinib hydrochloride obtained from Example 5

| Peak (degrees 2-theta) | Relative Intensity (%) |
|---|---|
| 23.33 | 11.91 |
| 23.93 | 32.70 |
| 24.18 | 19.90 |
| 24.81 | 6.38 |
| 25.00 | 4.08 |
| 25.57 | 27.88 |
| 25.79 | 17.79 |
| 27.75 | 11.71 |
| 28.49 | 19.95 |
| 29.37 | 9.45 |
| 29.79 | 7.24 |
| 30.37 | 6.42 |
| 30.61 | 12.23 |
| 31.52 | 7.78 |

In an embodiment, Form APO-C tofacitinib hydrochloride may be characterized by a PXRD comprising peaks, expressed in degrees 2-theta, at approximately 5.7±0.2, 11.4±0.2, 13.8±0.2, 14.4±0.2, 19.8±0.2, 21.6±0.2 and 22.8±0.2.

In an embodiment, Form APO-C tofacitinib hydrochloride comprises from about 15.2 wt % to about 21.2 wt % dimethyl sulfoxide.

Figure 6:
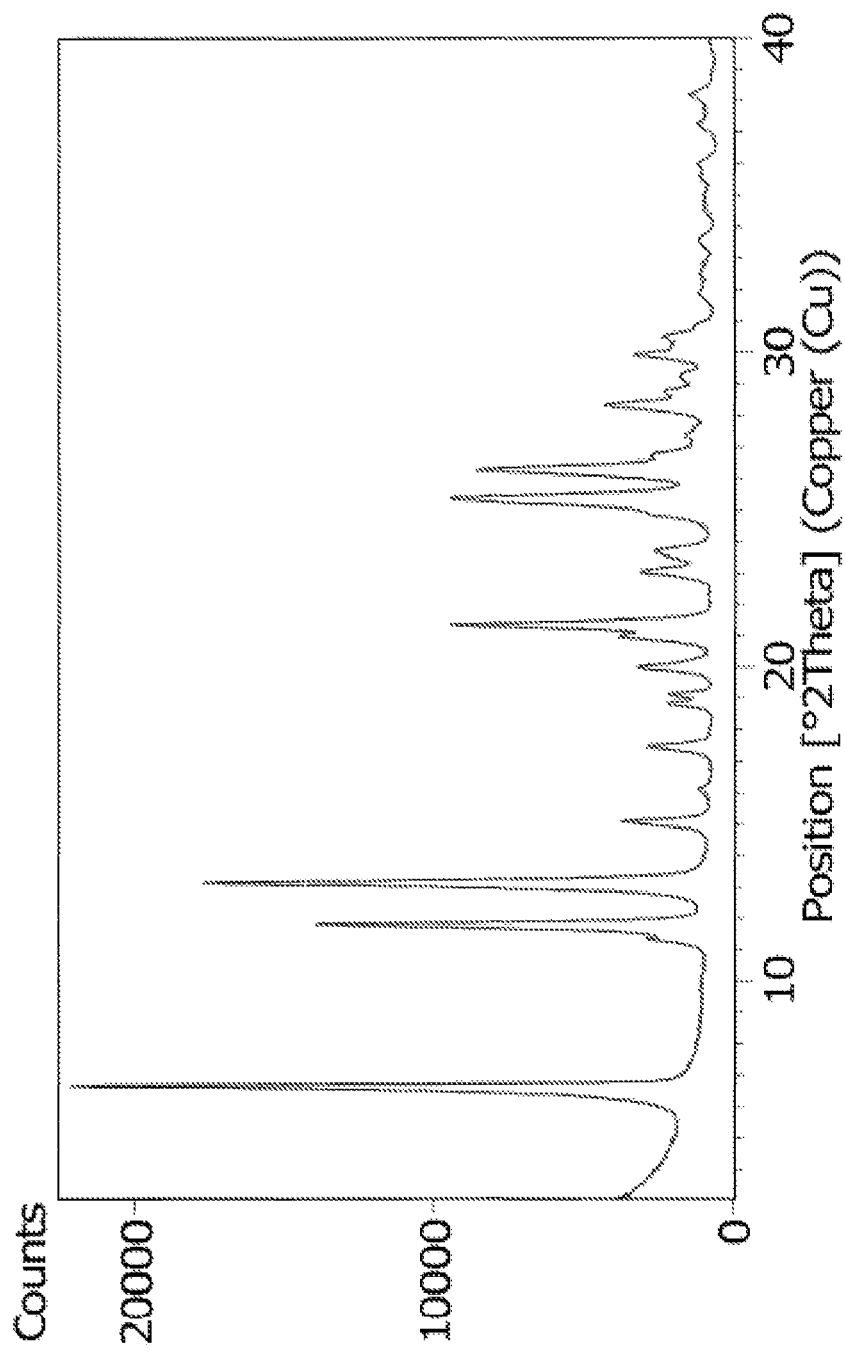
FIG. 6 is a Powder X-Ray Diffractogram (PXRD) of Form APO-D tofacitinib hydrochloride obtained according to Example 6.

An illustrative PXRD diffractogram of Form APO-D tofacitinib hydrochloride obtained according to the conditions given in Example 6 is shown in FIG. 6. According to FIG. 6, the Form APO-D tofacitinib hydrochloride may have a reflection ("peak") at any one or more of the values expressed in degrees 2-theta given in Table 6. Although values are given in the tables below, the form may be defined by the claimed peaks. Further, a particular claim may be limited to one peak only, or several peaks. The Form APO-D tofacitinib hydrochloride does not have to include all or even many of the peaks listed in Table 6. Some illustrative and non-limiting possible observations regarding relative intensities of the peaks are set out in Table 6.

TABLE 6

Form APO-D tofacitinib hydrochloride obtained from Example 6

| Peak (degrees 2-theta) | Relative Intensity (%) |
|---|---|
| 6.63 | 76.74 |
| 11.31 | 10.32 |
| 11.79 | 72.14 |
| 13.10 | 100.00 |
| 15.05 | 19.06 |
| 17.44 | 14.43 |
| 18.82 | 10.69 |
| 19.10 | 9.34 |
| 19.98 | 16.26 |
| 20.93 | 17.80 |
| 21.31 | 58.24 |
| 22.99 | 16.16 |
| 23.61 | 12.45 |
| 25.31 | 57.51 |
| 26.22 | 54.27 |
| 26.73 | 8.92 |
| 28.27 | 23.93 |
| 28.72 | 9.16 |
| 29.19 | 6.90 |
| 29.87 | 15.63 |
| 30.42 | 10.60 |

Figure 7:
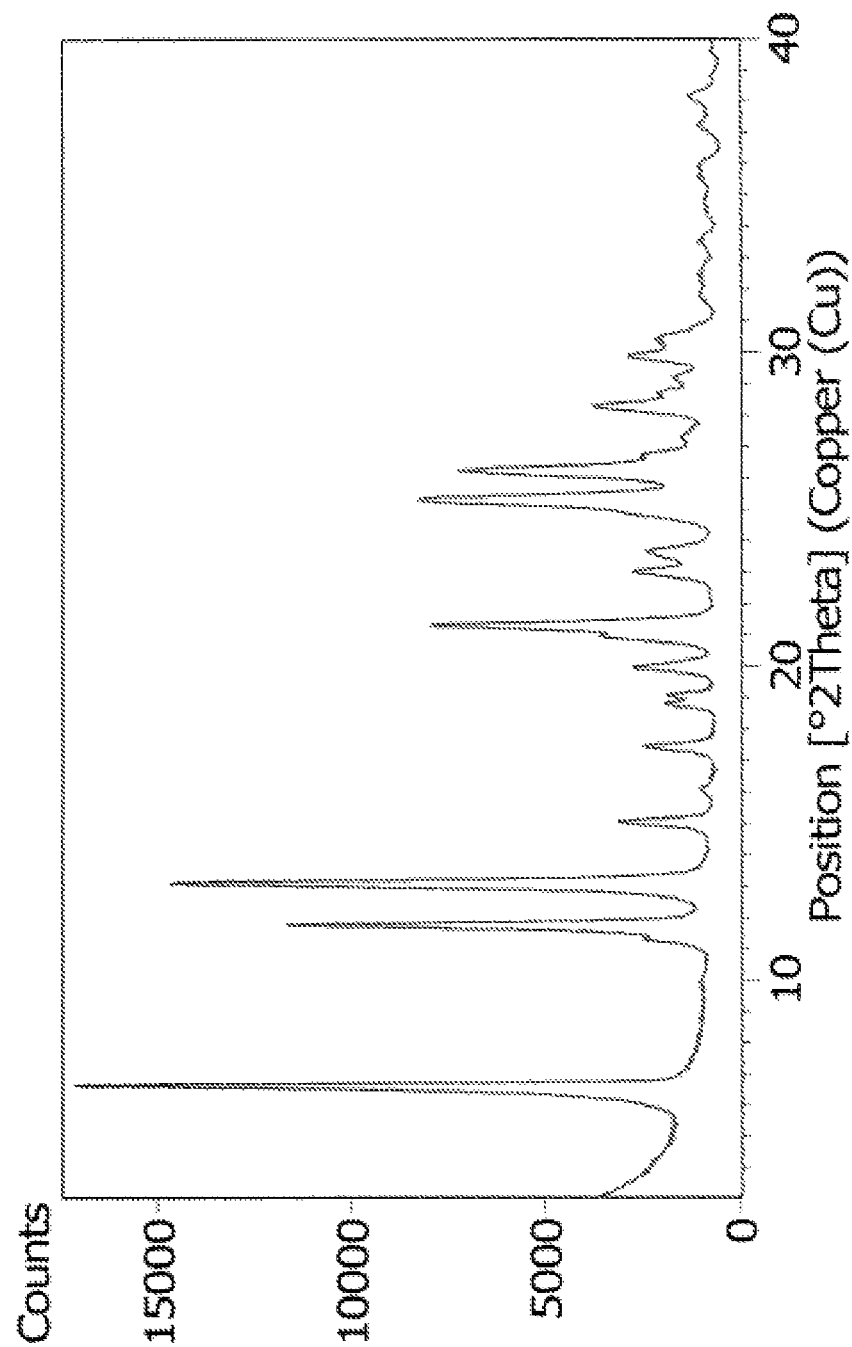
FIG. 7 is a Powder X-Ray Diffractogram (PXRD) of Form APO-D tofacitinib hydrochloride obtained according to Example 7.

An illustrative PXRD diffractogram of Form APO-D tofacitinib hydrochloride obtained according to the conditions given in Example 7 is shown in FIG. 7. According to FIG. 7, the Form APO-D tofacitinib hydrochloride may have a reflection ("peak") at any one or more of the values expressed in degrees 2-theta given in Table 7. Although values are given in the tables below, the form may be defined by the claimed peaks. Further, a particular claim may be limited to one peak only, or several peaks. The Form APO-D tofacitinib hydrochloride does not have to include all or even many of the peaks listed in Table 7. Some illustrative and non-limiting possible observations regarding relative intensities of the peaks are set out in Table 7.

TABLE 7

Form APO-D tofacitinib hydrochloride obtained from Example 7

| Peak (degrees 2-theta) | Relative Intensity (%) |
|---|---|
| 6.55 | 100.00 |
| 11.44 | 12.04 |
| 11.74 | 67.43 |
| 13.06 | 92.09 |
| 15.03 | 16.22 |
| 17.42 | 11.82 |
| 18.79 | 7.92 |
| 19.08 | 7.99 |
| 19.95 | 13.33 |
| 20.92 | 15.83 |
| 21.28 | 48.72 |
| 22.98 | 14.14 |
| 23.59 | 11.51 |
| 25.25 | 51.44 |
| 26.19 | 40.38 |
| 28.18 | 11.53 |
| 28.70 | 6.45 |
| 29.18 | 5.36 |
| 29.84 | 13.80 |
| 30.39 | 9.72 |

In an embodiment, Form APO-D tofacitinib hydrochloride may be characterized by a PXRD comprising peaks, expressed in degrees 2-theta, at approximately 6.6±0.2, 11.8±0.2, 17.4±0.2, 21.3±0.2, 25.3±0.2 and 26.2±0.2.

Figure 8:
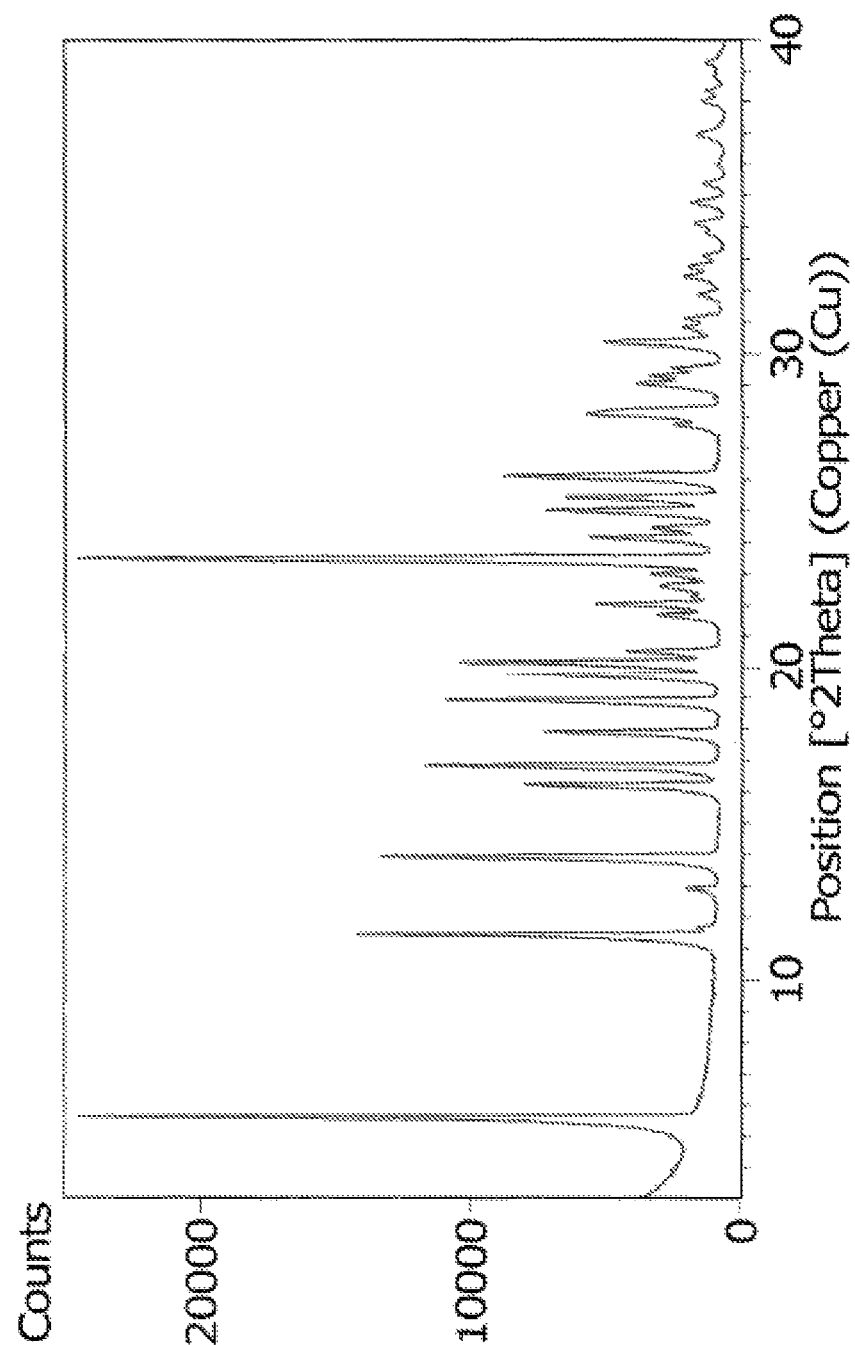
FIG. 8 is a Powder X-Ray Diffractogram (PXRD) of Form APO-E tofacitinib hydrochloride obtained according to Example 8.

An illustrative PXRD diffractogram of Form APO-E tofacitinib hydrochloride obtained according to the conditions given in Example 8 is shown in FIG. 8. According to FIG. 8, the Form APO-E tofacitinib hydrochloride may have a reflection ("peak") at any one or more of the values expressed in degrees 2-theta given in Table 8. Although values are given in the tables below, the form may be defined by the claimed peaks. Further, a particular claim may be limited to one peak only, or several peaks. The Form APO-E tofacitinib hydrochloride does not have to include all or even many of the peaks listed in Table 8. Some illustrative and non-limiting possible observations regarding relative intensities of the peaks are set out in Table 8.

TABLE 8

Form APO-E tofacitinib hydrochloride obtained from Example 8

| Peak (degrees 2-theta) | Relative Intensity (%) |
|---|---|
| 5.61 | 96.90 |
| 11.44 | 58.08 |
| 12.92 | 4.97 |
| 13.92 | 54.70 |
| 16.21 | 30.13 |
| 16.73 | 23.83 |
| 17.90 | 29.59 |
| 18.91 | 48.34 |
| 19.74 | 32.36 |
| 20.16 | 40.99 |
| 20.49 | 16.00 |
| 21.66 | 11.10 |
| 22.04 | 18.01 |

TABLE 8-continued

Form APO-E tofacitinib hydrochloride obtained from Example 8

| Peak (degrees 2-theta) | Relative Intensity (%) |
|---|---|
| 22.63 | 7.56 |
| 22.97 | 12.49 |
| 23.47 | 100.00 |
| 24.12 | 24.16 |
| 24.43 | 10.29 |
| 24.97 | 32.20 |
| 25.38 | 27.06 |
| 26.10 | 30.31 |
| 28.22 | 13.34 |
| 29.02 | 15.99 |
| 29.29 | 11.95 |
| 29.52 | 8.99 |
| 30.33 | 22.63 |

In an embodiment, Form APO-E tofacitinib hydrochloride may be characterized by a PXRD comprising peaks, expressed in degrees 2-theta, at approximately 5.6±0.2, 11.4±0.2, 16.3±0.2, 21.7±0.2, 23.5±0.2 and 28.2±0.2

In an embodiment, Form APO-E tofacitinib hydrochloride comprises from about 14.9 wt % to about 21.5 wt % N,N-dimethylacetamide.

Figure 9:
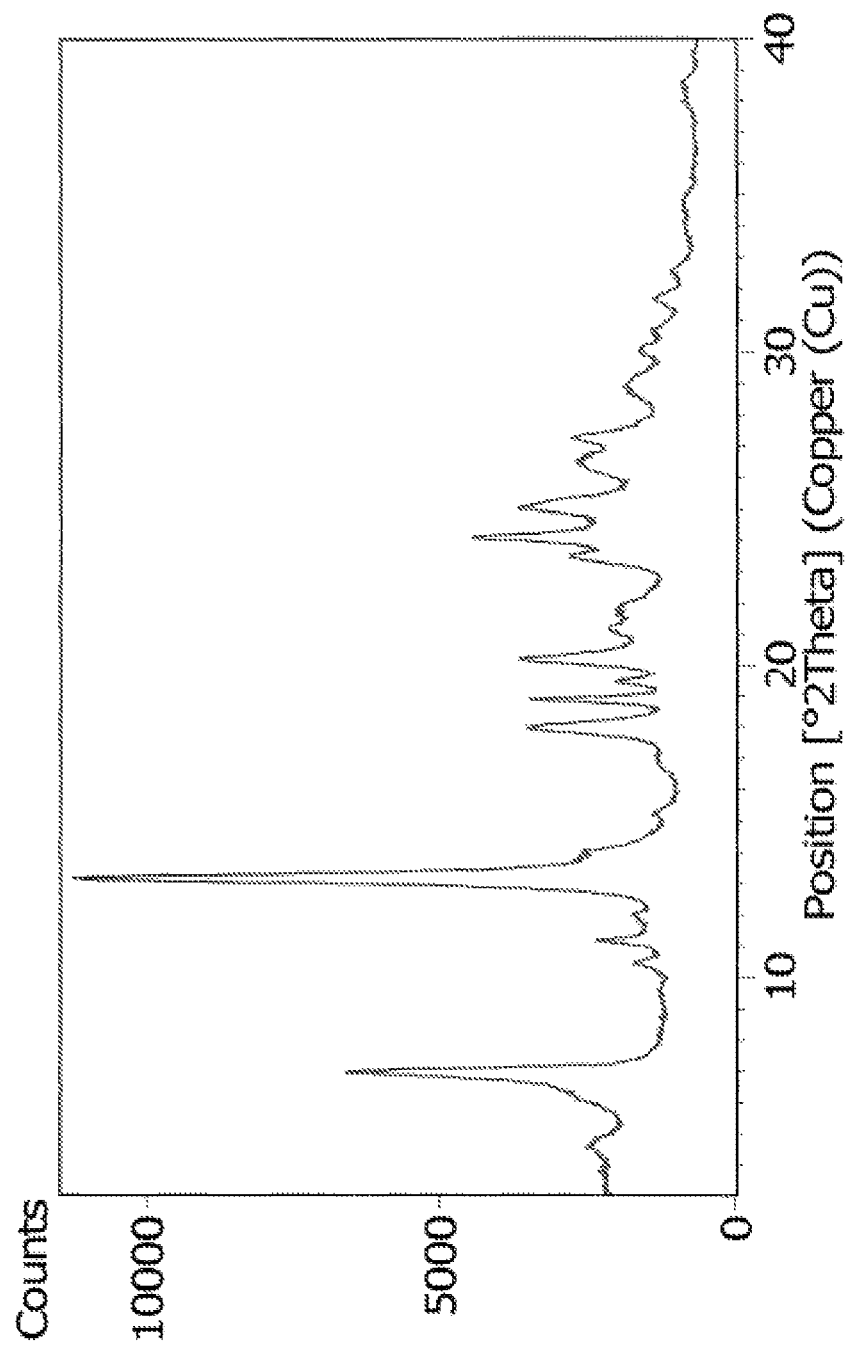
FIG. 9 is a Powder X-ray Diffractogram (PXRD) of Form APO-F tofacitinib hydrochloride obtained according to Example 9.

An illustrative PXRD diffractogram of Form APO-F tofacitinib hydrochloride obtained according to the conditions given in Example 9 is shown in FIG. 9. According to FIG. 9, the Form APO-F tofacitinib hydrochloride may have a reflection ("peak") at any one or more of the values expressed in degrees 2-theta given in Table 9. Although values are given in the tables below, the form may be defined by the claimed peaks. Further, a particular claim may be limited to one peak only, or several peaks. The Form APO-F tofacitinib hydrochloride does not have to include all or even many of the peaks listed in Table 9. Some illustrative and non-limiting possible observations regarding relative intensities of the peaks are set out in Table 9.

TABLE 9

Form APO-F tofacitinib hydrochloride obtained from Example 9

| Peak (degrees 2-theta) | Relative Intensity (%) |
|---|---|
| 6.94 | 41.94 |
| 10.44 | 4.61 |
| 11.17 | 10.95 |
| 13.16 | 100.00 |
| 17.95 | 24.99 |
| 18.87 | 23.87 |
| 19.44 | 7.61 |
| 20.21 | 22.06 |
| 23.44 | 13.71 |
| 24.07 | 31.24 |
| 25.05 | 24.50 |
| 26.43 | 15.01 |
| 27.27 | 15.34 |
| 28.88 | 9.30 |

In an embodiment, Form APO-F tofacitinib hydrochloride may be characterized by a PXRD comprising peaks, expressed in degrees 2-theta, at approximately 6.9±0.2, 13.2±0.2, 17.9±0.2, 18.9±0.2, 20.2±0.2 and 24.1±0.2

Figure 10:
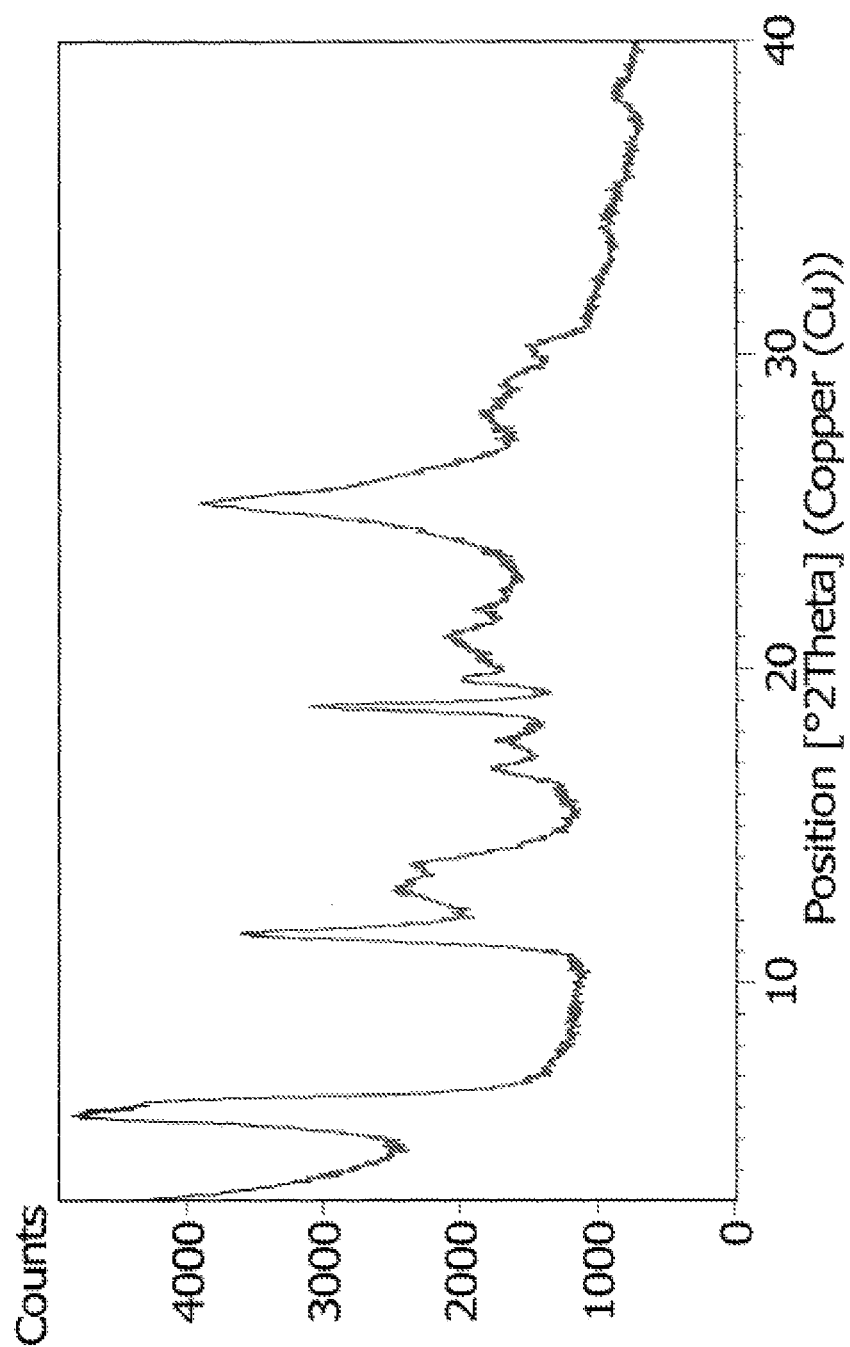
FIG. 10 is a Powder X-Ray Diffractogram (PXRD) of Form APO-G tofacitinib hydrochloride obtained according to Example 10.

An illustrative PXRD diffractogram of Form APO-G tofacitinib hydrochloride obtained according to the conditions given in Example 10 is shown in FIG. 10. According to FIG. 10, the Form APO-G tofacitinib hydrochloride may have a reflection ("peak") at any one or more of the values expressed in degrees 2-theta given in Table 10. Although values are given in the tables below, the form may be defined by the claimed peaks. Further, a particular claim may be limited to one peak only, or several peaks. The Form APO-G tofacitinib hydrochloride does not have to include all or even many of the peaks listed in Table 10. Some illustrative and non-limiting possible observations regarding relative intensities of the peaks are set out in Table 10.

TABLE 10

Form APO-G tofacitinib hydrochloride obtained from Example 10

| Peak (degrees 2-theta) | Relative Intensity (%) |
|---|---|
| 5.65 | 94.74 |
| 6.10 | 100.00 |
| 11.53 | 85.20 |
| 12.97 | 32.49 |
| 13.80 | 26.55 |
| 16.77 | 21.58 |
| 17.70 | 17.20 |
| 18.77 | 72.61 |
| 19.64 | 21.83 |
| 20.79 | 31.14 |
| 25.27 | 88.63 |
| 30.23 | 12.71 |

In an embodiment, Form APO-G tofacitinib hydrochloride may be characterized by a PXRD comprising peaks, expressed in degrees 2-theta, at approximately 6.1±0.2, 11.5±0.2, 13.0±0.2, 16.7±0.2, 18.8±0.2 and 20.8±0.2.

In an embodiment, Form APO-G tofacitinib hydrochloride comprises from about 7.6 to about 11.0 wt % methyl ethyl ketone.

Figure 11:
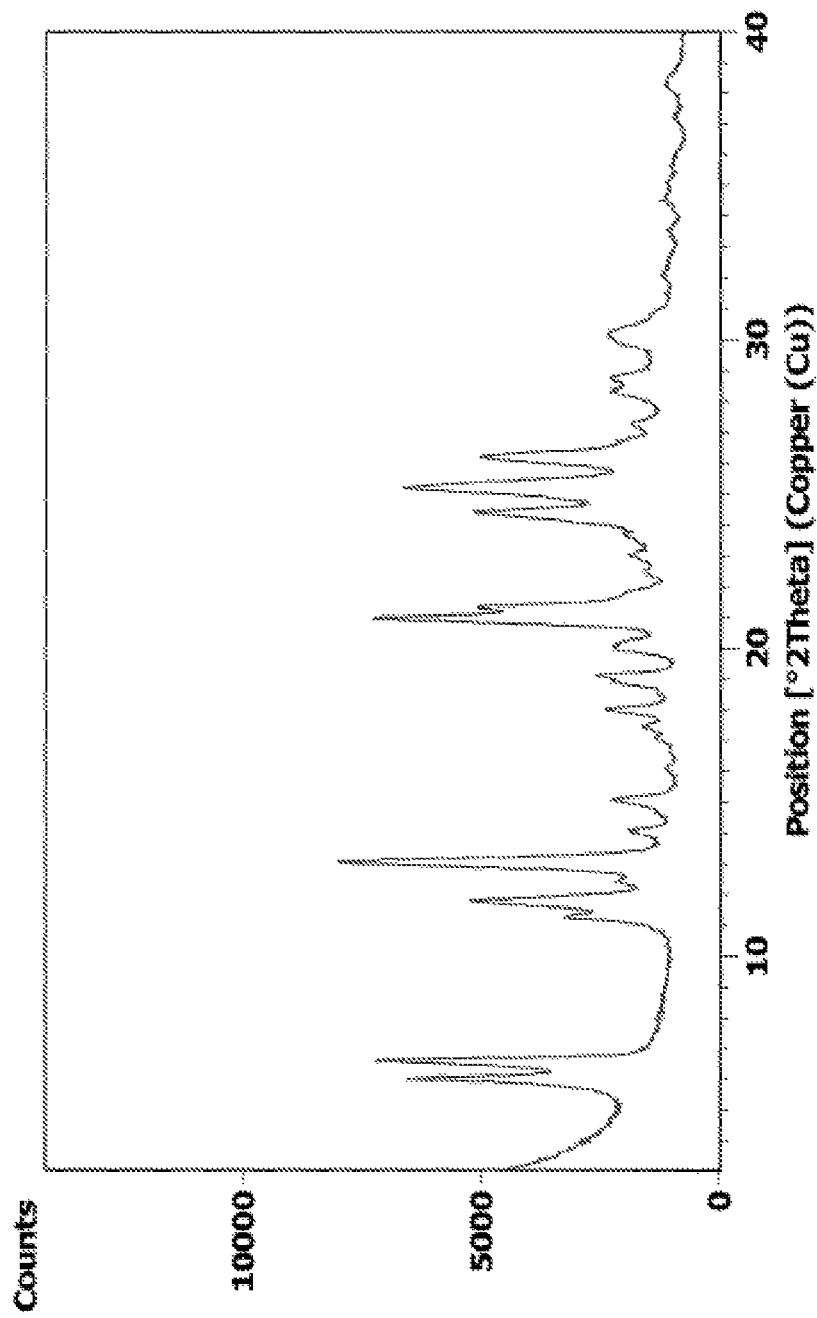
FIG. 11 is a Powder X-Ray Diffractogram (PXRD) of Form APO-H tofacitinib hydrochloride obtained according to Example 25.

An illustrative PXRD diffractogram of Form APO-H tofacitinib hydrochloride obtained according to the conditions given in Example 25 is shown in FIG. 11. According to FIG. 11, the Form APO-H tofacitinib hydrochloride may have a reflection ("peak") at any one or more of the values expressed in degrees 2-theta given in Table 11. Although values are given in the tables below, the form may be defined by the claimed peaks. Further, a particular claim may be limited to one peak only, or several peaks. The Form APO-H tofacitinib hydrochloride does not have to include all or even many of the peaks listed in Table 11. Some illustrative and non-limiting possible observations regarding relative intensities of the peaks are set out in Table 11.

TABLE 11

Form APO-H tofacitinib hydrochloride obtained from Example 25

| Peak (degrees 2-theta) | Relative Intensity (%) |
|---|---|
| 6.00 | 39.55 |
| 6.60 | 58.58 |
| 11.27 | 29.50 |
| 11.76 | 54.62 |
| 12.43 | 11.45 |
| 13.05 | 100.00 |
| 14.05 | 11.88 |
| 15.04 | 18.53 |
| 16.10 | 2.44 |
| 17.07 | 4.44 |
| 17.44 | 8.33 |
| 17.99 | 20.30 |
| 19.11 | 20.29 |
| 19.98 | 14.98 |
| 20.94 | 85.28 |
| 21.31 | 51.74 |
| 24.31 | 46.34 |
| 25.18 | 71.59 |
| 26.18 | 56.87 |
| 27.26 | 10.25 |
| 28.27 | 15.08 |

TABLE 11-continued

Form APO-H tofacitinib hydrochloride obtained from Example 25

| Peak (degrees 2-theta) | Relative Intensity (%) |
|---|---|
| 28.74 | 16.77 |
| 30.12 | 19.77 |

In an embodiment, Form APO-H tofacitinib hydrochloride may be characterized by a PXRD comprising peaks, expressed in degrees 2-theta, at approximately 5.9±0.2, 6.6±0.2, 13.0±0.2, 14.0±0.2, 15.0±0.2 and 20.9±0.2.

Process for preparing crystalline forms of tofacitinib hydrochloride are also provided. In one embodiment, preparation of a crystalline form of tofacitinib hydrochloride comprises:
a) combining hydrogen chloride with a mixture of tofacitinib free base and an organic solvent selected from the group consisting of $C_3$-$C_7$ ketones, N,N-dialkylamides, alkyl nitriles, alkyl sulfoxides and nitroalkanes thereby obtaining a precipitate; and
b) isolating the precipitate to yield crystalline tofacitinib hydrochloride.

The organic solvent may be selected from $C_3$-$C_7$ ketones, such as acetone and methyl ethyl ketone, N,N-dialkylamides, such as N,N-dimethylformamide and N,N-dimethylacetamide, alkyl nitriles such as acetonitrile, alkyl sulfoxides such as dimethylsulfoxide and nitroalkanes such as nitromethane.

In the process, hydrogen chloride may be provided as a solution of hydrogen chloride in an organic solvent. In such embodiments, the organic solvent is often 1,4-dioxane or isopropanol. In some embodiments, the hydrogen chloride may be provided as an aqueous solution.

In some embodiments, the isolating is carried out by filtration. In other embodiments, the isolating is carried out by evaporating the solvent.

In another embodiment, preparation of a crystalline form of tofacitinib hydrochloride comprises:
a) suspending amorphous tofacitinib hydrochloride in an organic solvent selected from the group consisting of $C_3$-$C_7$ ketones, N,N-dialkylamides, alkyl nitriles, alkyl sulfoxides and nitroalkanes thereby obtaining a precipitate; and
b) isolating the precipitate to yield crystalline tofacitinib hydrochloride.

The organic solvent may be selected from $C_3$-$C_7$ ketones, such as acetone and methyl ethyl ketone, N,N-dialkylamides, such as N,N-dimethylformamide and N,N-dimethylacetamide, alkyl nitriles such as acetonitrile, alkyl sulfoxides such as dimethylsulfoxide and nitroalkanes such as nitromethane.

In some embodiments, the isolating is carried out by filtration. In other embodiments, the isolating is carried out by evaporating the solvent.

In other embodiments, preparation of tofacitinib citrate is provided. In one embodiment, preparation of tofacitinib citrate comprises combining tofacitinib hydrochloride with a dihydrogen citrate salt. In one embodiment, the combining is done in water and the dihydrogen citrate salt consists of dihydrogen citrate and a counterion whereby the counterion forms a salt with the chloride ion of the tofacitinib hydrochloride that is substantially water soluble. The dihydrogen citrate salt may be an alkali metal dihydrogen citrate salt, for example and without limitation, monosodium citrate salt, as well as other alkali metal citrate salts, such as monolithum citrate, and monopotassium citrate. In some of these embodiments the dihydrogen citrate salt may be prepared in situ by reacting citric acid with a base in the presence of tofacitinib hydrochloride.

The base used to prepare the dihydrogen citrate salt in situ may be an organic base or an inorganic base with a pKa (conjugate acid) higher than that of citric acid. Inorganic bases may be, without limitation, a metal hydroxide, a metal carbonate, a metal bicarbonate, or mixtures thereof. Organic bases may be, without limitation, organic amines including ammonia, primary amines, secondary amines and tertiary amines. For example, suitable bases include, but are not limited to, lithium hydroxide monohydrate, sodium bicarbonate, potassium carbonate, N,N-Diisopropylethylamine, N,N-Diisopropylamine, cesium carbonate, potassium acetate, ammonium acetate, n-butylamine, 1,8-diazabicycloundec-7-ene (DBU), and ammonium hydroxide.

In another embodiment, preparation of tofacitinib citrate comprises combining tofacitinib hydrochloride with citric acid.

In one embodiment, the present invention comprises Form APO-I tofacitinib hydrobromide.

Figure 13:
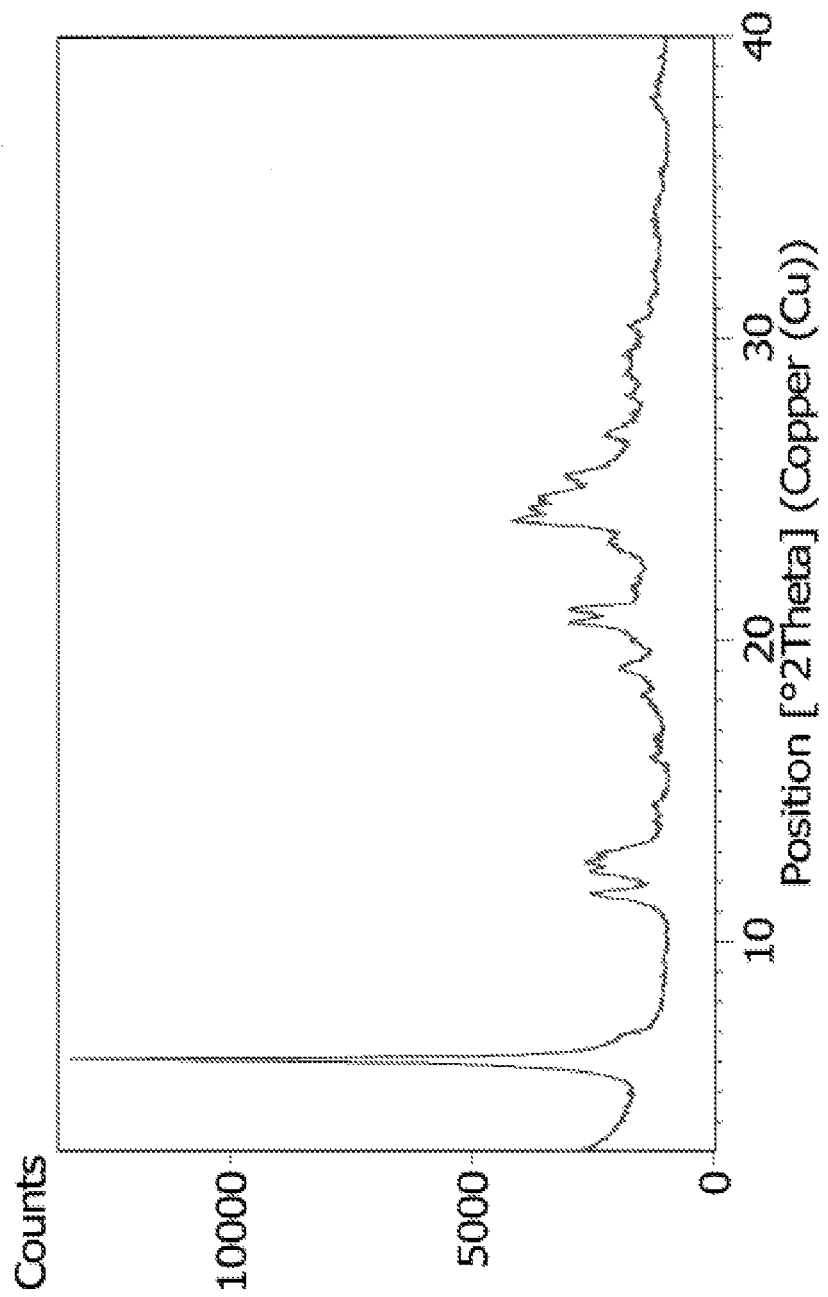
FIG. 13 is a Powder X-Ray Diffractogram (PXRD) of Form APO-I tofacitinib hydrobromide obtained according to Example 37.

An illustrative PXRD diffractogram of Form APO-I tofacitinib hydrobromide obtained according to the conditions given in Example 37 is shown in FIG. 13. According to FIG. 13, the Form APO-I tofacitinib hydrobromide may have a reflection ("peak") at any one or more of the values expressed in degrees 2-theta given in Table 12. Although values are given in the tables below, the form may be defined by the claimed peaks. Further, a particular claim may be limited to one peak only, or several peaks. The Form APO-I tofacitinib hydrobromide does not have to include all or even many of the peaks listed in Table 12. Some illustrative and non-limiting possible observations regarding relative intensities of the peaks are set out in Table 12.

TABLE 12

Form APO-I tofacitinib hydrobromide obtained from Example 37

| Peak (degrees 2-theta) | Relative Intensity (%) |
|---|---|
| 6.08 | 100.00 |
| 11.56 | 19.66 |
| 12.34 | 16.53 |
| 12.64 | 9.21 |
| 12.90 | 17.57 |
| 18.12 | 5.31 |
| 19.09 | 11.55 |
| 20.59 | 21.90 |
| 21.00 | 21.24 |
| 23.21 | 11.96 |
| 23.89 | 27.30 |
| 24.05 | 11.23 |
| 24.33 | 27.08 |
| 24.74 | 20.90 |
| 25.40 | 23.79 |
| 26.86 | 11.71 |
| 28.10 | 6.54 |

In an embodiment, Form APO-I tofacitinib hydrobromide may be characterized by a PXRD comprising peaks, expressed in degrees 2-theta, at approximately 6.1±0.2, 12.6±0.2, 19.1±0.2, 21.0±0.2, 23.9±0.2 and 25.4±0.2.

In an embodiment, Form APO-I tofacitinib hydrobromide comprises from about 4.1 wt % to about 6.0 wt % acetonitrile.

Figure 14:
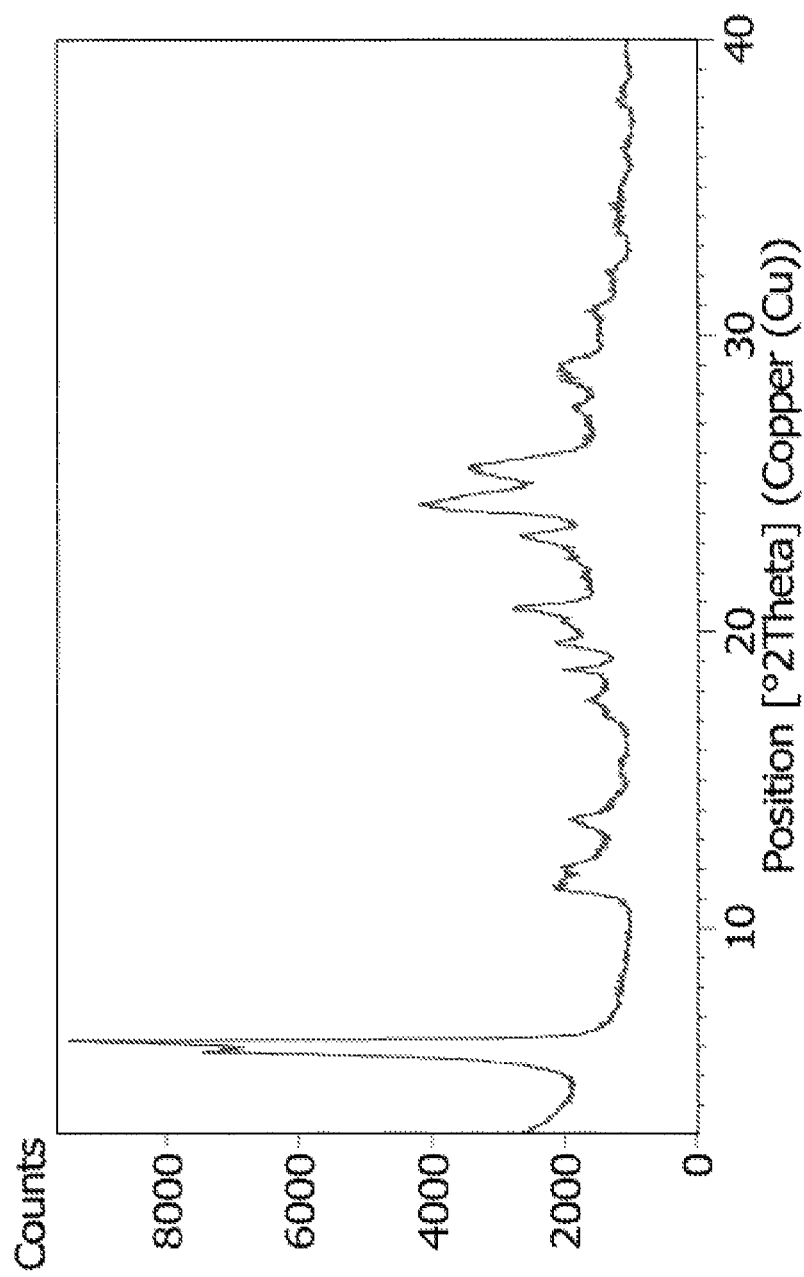
FIG. 14 is a Powder X-Ray Diffractogram (PXRD) of Form APO-J tofacitinib hydrobromide obtained according to Example 38.

An illustrative PXRD diffractogram of Form APO-J tofacitinib hydrobromide obtained according to the conditions given in Example 38 is shown in FIG. 14. According to FIG. 14, the Form APO-J tofacitinib hydrobromide may have a reflection ("peak") at any one or more of the values expressed in degrees 2-theta given in Table 13. Although values are given in the tables below, the form may be defined by the claimed peaks. Further, a particular claim may be limited to one peak only, or several peaks. The Form APO-J tofacitinib hydrobromide does not have to include all or even many of the peaks listed in Table 13. Some illustrative and non-limiting possible observations regarding relative intensities of the peaks are set out in Table 13.

TABLE 13

Form APO-J tofacitinib hydrobromide obtained from Example 38

| Peak (degrees 2-theta) | Relative Intensity (%) |
|---|---|
| 5.83 | 100.00 |
| 6.12 | 99.81 |
| 11.38 | 12.16 |
| 11.97 | 14.25 |
| 13.62 | 11.88 |
| 17.77 | 6.91 |
| 18.72 | 11.21 |
| 19.72 | 11.98 |
| 20.73 | 22.29 |
| 23.20 | 12.21 |
| 24.29 | 23.56 |
| 25.47 | 35.38 |
| 27.48 | 9.60 |
| 28.99 | 13.64 |

In an embodiment, Form APO-J tofacitinib hydrobromide may be characterized by a PXRD comprising peaks, expressed in degrees 2-theta, at approximately 6.1±0.2, 12.0±0.2, 13.6±0.2, 19.7±0.2, 20.8±0.2 and 25.5±0.2.

In an embodiment, Form APO-J tofacitinib hydrobromide comprises from about 4.8 wt % to about 7.1 wt % acetone.

Figure 15:
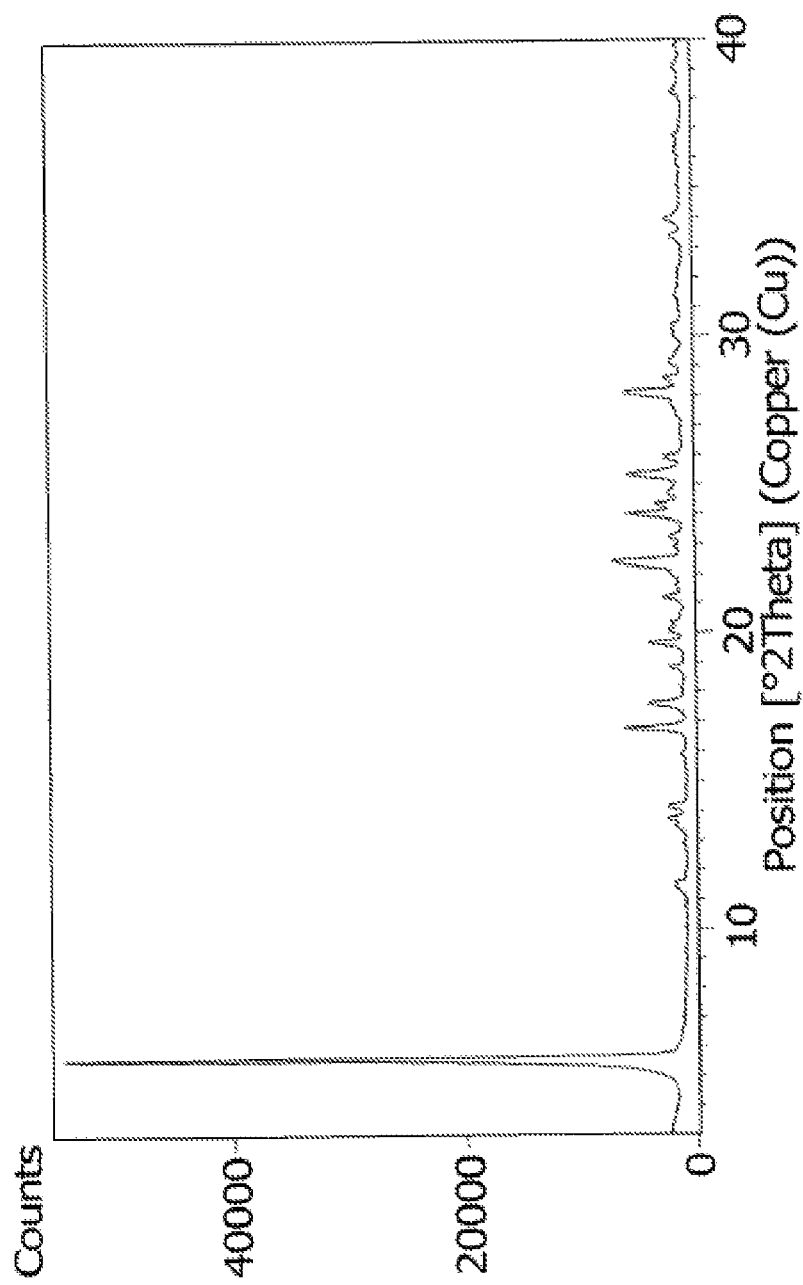
FIG. 15 is a Powder X-Ray Diffractogram (PXRD) of Form APO-K tofacitinib hydrobromide obtained according to Example 39.

An illustrative PXRD diffractogram of Form APO-K tofacitinib hydrobromide obtained according to the conditions given in Example 39 is shown in FIG. 15. According to FIG. 15, the Form APO-K tofacitinib hydrobromide may have a reflection ("peak") at any one or more of the values expressed in degrees 2-theta given in Table 14. Although values are given in the tables below, the form may be defined by the claimed peaks. Further, a particular claim may be limited to one peak only, or several peaks. The Form APO-K tofacitinib hydrobromide does not have to include all or even many of the peaks listed in Table 14. Some illustrative and non-limiting possible observations regarding relative intensities of the peaks are set out in Table 14.

TABLE 14

Form APO-K tofacitinib hydrobromide obtained from Example 39

| Peak (degrees 2-theta) | Relative Intensity (%) |
|---|---|
| 5.60 | 100.00 |
| 11.41 | 2.55 |
| 11.57 | 1.66 |
| 13.47 | 2.17 |
| 13.72 | 3.96 |
| 14.12 | 3.91 |
| 16.76 | 13.38 |
| 17.59 | 8.29 |
| 18.82 | 3.39 |
| 19.64 | 7.92 |
| 20.06 | 3.13 |
| 20.31 | 2.76 |
| 21.18 | 4.76 |
| 22.30 | 13.06 |
| 22.89 | 1.53 |
| 23.20 | 2.62 |
| 23.97 | 12.52 |
| 24.30 | 5.38 |
| 24.70 | 3.02 |

TABLE 14-continued

Form APO-K tofacitinib hydrobromide obtained from Example 39

| Peak (degrees 2-theta) | Relative Intensity (%) |
|---|---|
| 25.31 | 13.06 |
| 25.90 | 4.11 |
| 28.07 | 13.12 |

In an embodiment, Form APO-K tofacitinib hydrobromide may be characterized by a PXRD comprising peaks, expressed in degrees 2-theta, at approximately 5.6±0.2, 16.8±0.2, 21.2±0.2, 22.3±0.2, 24.0±0.2 and 24.7±0.2.

In an embodiment, Form APO-K tofacitinib hydrobromide comprises from about 10.4 wt % to about 14.8 wt % N,N-dimethylformamide.

Figure 16:
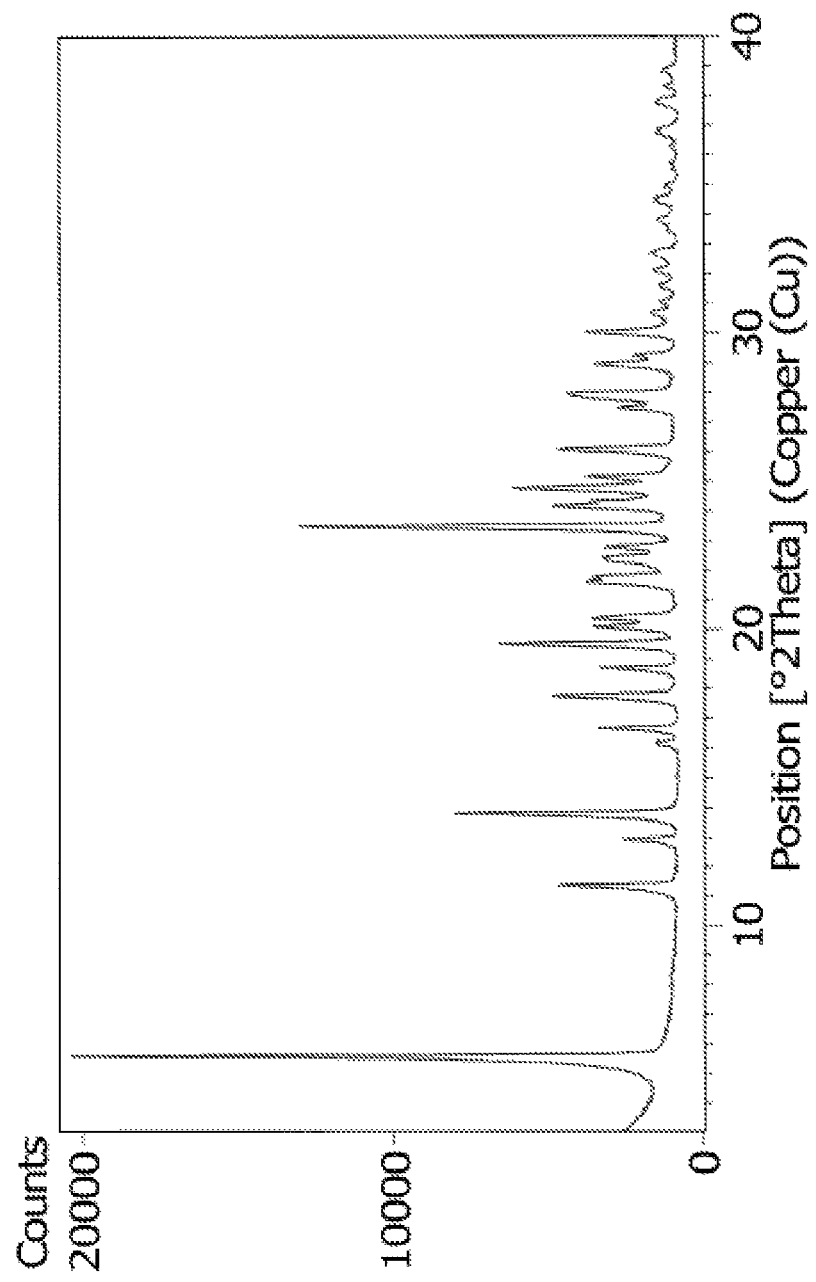
FIG. 16 is a Powder X-Ray Diffractogram (PXRD) of Form APO-L tofacitinib hydrobromide obtained according to Example 40.

An illustrative PXRD diffractogram of Form APO-L tofacitinib hydrobromide obtained according to the conditions given in Example 40 is shown in FIG. 16. According to FIG. 16, the Form APO-L tofacitinib hydrobromide may have a reflection ("peak") at any one or more of the values expressed in degrees 2-theta given in Table 15. Although values are given in the tables below, the form may be defined by the claimed peaks. Further, a particular claim may be limited to one peak only, or several peaks. The Form APO-L tofacitinib hydrobromide does not have to include all or even many of the peaks listed in Table 15. Some illustrative and non-limiting possible observations regarding relative intensities of the peaks are set out in Table 15.

TABLE 15

Form APO-L tofacitinib hydrobromide obtained from Example 40

| Peak (degrees 2-theta) | Relative Intensity (%) |
|---|---|
| 5.59 | 100.00 |
| 11.36 | 25.71 |
| 12.92 | 13.23 |
| 13.81 | 47.73 |
| 16.16 | 5.83 |
| 16.67 | 19.03 |
| 17.74 | 30.27 |
| 18.68 | 18.44 |
| 19.52 | 36.31 |
| 20.09 | 18.95 |
| 20.39 | 19.81 |
| 21.61 | 20.90 |
| 21.79 | 13.00 |
| 22.32 | 14.55 |
| 22.77 | 14.71 |
| 23.47 | 72.66 |
| 24.14 | 26.53 |
| 24.32 | 12.50 |
| 24.75 | 38.55 |
| 25.13 | 19.83 |
| 26.05 | 28.27 |
| 27.47 | 13.01 |
| 27.82 | 20.91 |
| 28.93 | 19.54 |
| 29.23 | 8.89 |
| 30.02 | 21.85 |

In an embodiment, Form APO-L tofacitinib hydrobromide may be characterized by a PXRD comprising peaks, expressed in degrees 2-theta, at approximately 5.6±0.2, 16.2±0.2, 17.7±0.2, 21.6±0.2, 23.5±0.2 and 25.1±0.2.

In an embodiment, Form APO-L tofacitinib hydrobromide comprises from about 12.5 wt % to about 17.7 wt % N,N-dimethylacetamide.

Figure 17:
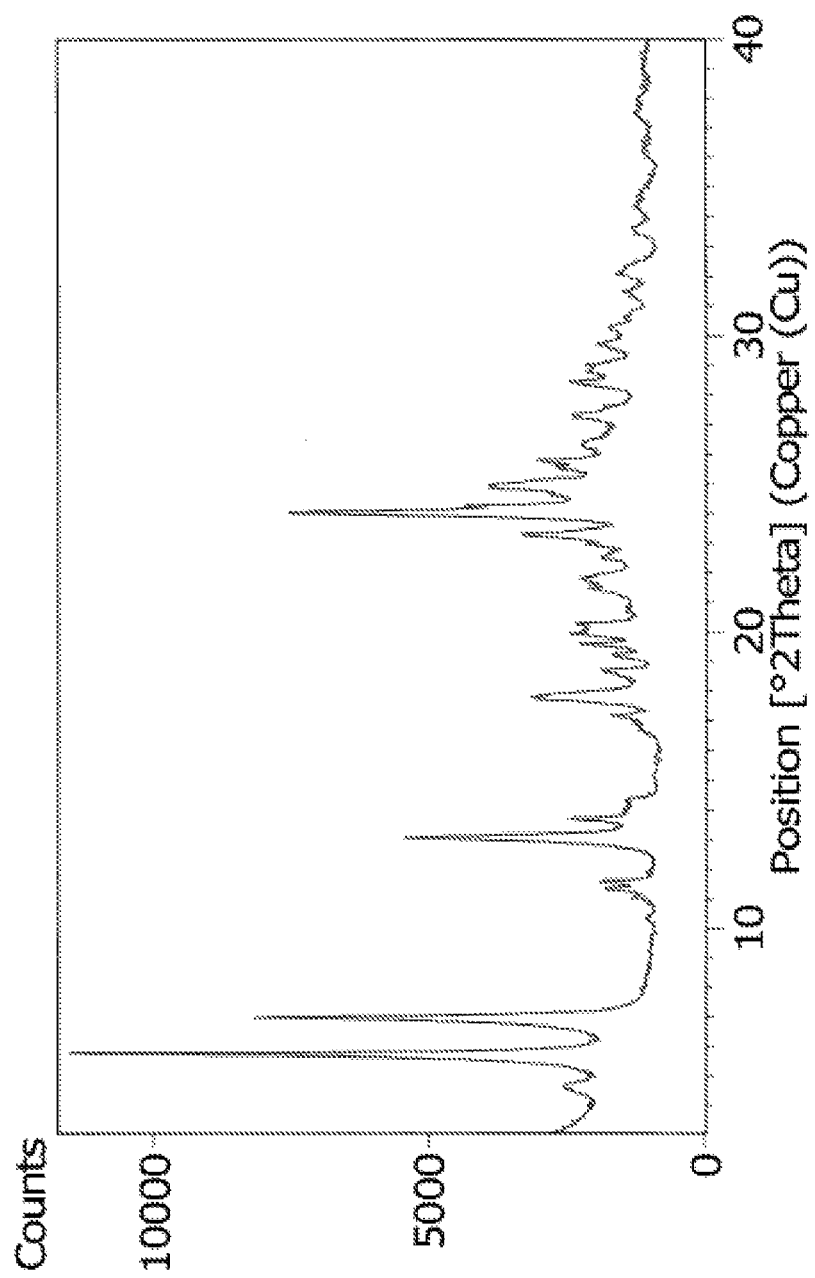
FIG. 17 is a Powder X-Ray Diffractogram (PXRD) of Form APO-M tofacitinib hydrobromide obtained according to Example 41.

An illustrative PXRD diffractogram of Form APO-M tofacitinib hydrobromide obtained according to the conditions given in Example 41 is shown in FIG. 17. According to FIG. 17, the Form APO-M tofacitinib hydrobromide may have a reflection ("peak") at any one or more of the values expressed in degrees 2-theta given in Table 16. Although values are given in the tables below, the form may be defined by the claimed peaks. Further, a particular claim may be limited to one peak only, or several peaks. The Form APO-M tofacitinib hydrobromide does not have to include all or even many of the peaks listed in Table 16. Some illustrative and non-limiting possible observations regarding relative intensities of the peaks are set out in Table 16.

TABLE 16

Form APO-M tofacitinib hydrobromide obtained from Example 41

| Peak (degrees 2-theta) | Relative Intensity (%) |
|---|---|
| 5.74 | 100.00 |
| 6.95 | 79.39 |
| 11.33 | 12.92 |
| 11.57 | 13.74 |
| 13.06 | 68.18 |
| 13.69 | 19.47 |
| 17.08 | 3.59 |
| 17.81 | 33.81 |
| 18.62 | 11.01 |
| 19.20 | 9.16 |
| 19.56 | 14.58 |
| 20.03 | 18.87 |
| 20.27 | 9.96 |
| 21.82 | 5.90 |
| 22.55 | 9.48 |
| 23.26 | 29.14 |
| 24.00 | 89.40 |
| 24.90 | 38.36 |
| 25.75 | 22.63 |
| 26.35 | 13.91 |
| 27.30 | 16.56 |
| 28.38 | 16.08 |
| 28.88 | 14.47 |

In an embodiment, Form APO-M tofacitinib hydrobromide may be characterized by a PXRD comprising peaks, expressed in degrees 2-theta, at approximately 5.7±0.2, 6.9±0.2, 13.1±0.2, 17.8±0.2, 24.0±0.2 and 24.9±0.2.

In an embodiment, Form APO-M tofacitinib hydrobromide comprises from about 4.4 wt % to about 6.5 wt % acetone.

Figure 18:
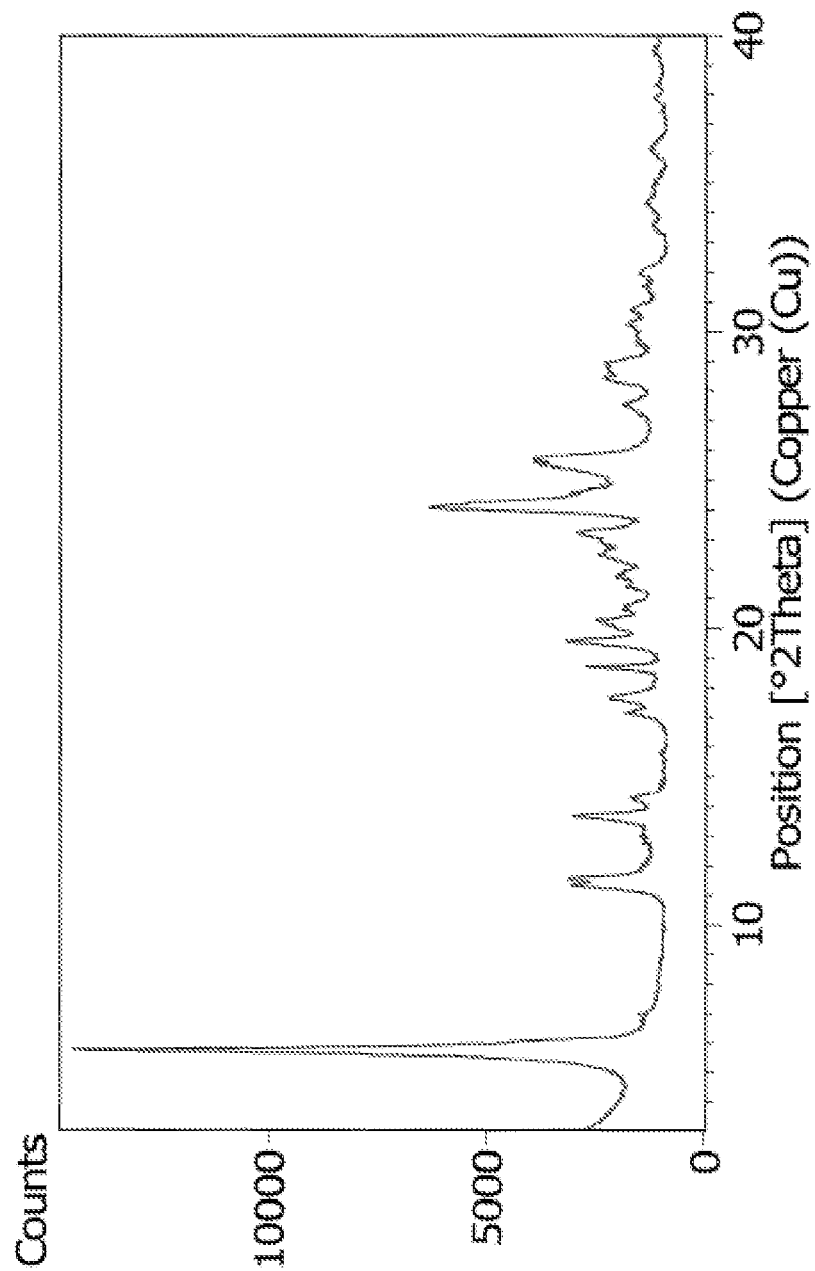
FIG. 18 is a Powder X-Ray Diffractogram (PXRD) of Form APO-N tofacitinib hydrobromide obtained according to Example 42.

An illustrative PXRD diffractogram of Form APO-N tofacitinib hydrobromide obtained according to the conditions given in Example 42 is shown in FIG. 18. According to FIG. 18, the Form APO-N tofacitinib hydrobromide may have a reflection ("peak") at any one or more of the values expressed in degrees 2-theta given in Table 17. Although values are given in the tables below, the form may be defined by the claimed peaks. Further, a particular claim may be limited to one peak only, or several peaks. The Form APO-N tofacitinib hydrobromide does not have to include all or even many of the peaks listed in Table 17. Some illustrative and non-limiting possible observations regarding relative intensities of the peaks are set out in Table 17.

TABLE 17

Form APO-N tofacitinib hydrobromide obtained from Example 42

| Peak (degrees 2-theta) | Relative Intensity (%) |
|---|---|
| 5.74 | 100.00 |
| 11.30 | 12.45 |
| 11.56 | 16.47 |
| 13.67 | 15.50 |

TABLE 17-continued

Form APO-N tofacitinib hydrobromide obtained from Example 42

| Peak (degrees 2-theta) | Relative Intensity (%) |
|---|---|
| 14.27 | 4.93 |
| 17.14 | 6.71 |
| 17.67 | 10.79 |
| 18.69 | 14.14 |
| 19.55 | 17.83 |
| 20.20 | 11.87 |
| 20.78 | 5.77 |
| 21.41 | 5.97 |
| 21.80 | 8.15 |
| 22.49 | 11.85 |
| 23.20 | 13.48 |
| 24.11 | 29.72 |
| 25.59 | 22.59 |
| 27.47 | 5.48 |
| 28.86 | 9.38 |

In an embodiment, Form APO-N tofacitinib hydrobromide may be characterized by a PXRD comprising peaks, expressed in degrees 2-theta, at approximately 5.7±0.2, 13.7±0.2, 14.3±0.2, 20.8±0.2, 21.4±0.2 and 27.5±0.2.

In an embodiment, Form APO-N tofacitinib hydrobromide comprises from about 7.6 wt % to about 11.0 wt % acetone.

Processes for preparing crystalline forms of tofacitinib hydrobromide are also provided. In one embodiment, preparation of a crystalline form of tofacitinib hydrobromide comprises:

a) suspending amorphous tofacitinib hydrobromide in an organic solvent selected from the group consisting of acetone, alkyl nitriles and mixtures of N,N-dialkylamides with alkyl esters thereby obtaining a precipitate; and b) isolating the precipitate to yield crystalline tofacitinib hydrobromide.

The organic solvent may be selected from acetone, alkyl nitriles such as acetonitrile and mixtures of N,N-dialkylamides, such as N,N-dimethylformamide and N,N-dimethylacetamide with alkyl esters such as ethyl acetate.

In one embodiment, preparation of a crystalline form of tofacitinib hydrobromide comprises:

a) combining hydrogen bromide with a mixture of tofacitinib free base and an organic solvent selected from the group consisting of acetone, alkyl nitriles and mixtures of N,N-dialkylamides with alkyl esters thereby obtaining a precipitate; and b) isolating the precipitate to yield crystalline tofacitinib hydrobromide.

The organic solvent may be selected from acetone, alkyl nitriles such as acetonitrile and mixtures of N,N-dialkylamides, such as N,N-dimethylformamide and N,N-dimethylacetamide with alkyl esters such as ethyl acetate.

In the process, hydrogen bromide may be provided as a solution of hydrogen bromide in an organic solvent. In such embodiments, the organic solvent is often 1,4-dioxane or isopropanol. In some embodiments, the hydrogen bromide may be provided as an aqueous solution.

In other embodiments, preparation of tofacitinib citrate is provided. In one embodiment, preparation of tofacitinib citrate comprises combining tofacitinib hydrobromide with a dihydrogen citrate salt. In one embodiment, the combining is done in water and the dihydrogen citrate salt consists of dihydrogen citrate and a counterion whereby the counterion forms a salt with the bromide ion of the tofacitinib hydrobromide that is substantially water soluble. The dihydrogen citrate salt may be an alkali metal dihydrogen citrate salt, for example and without limitation, monosodium citrate salt, as well as other alkali metal citrate salts, such as monolithum citrate, and monopotassium citrate. In some of these embodiments the dihydrogen citrate salt may be prepared in situ by reacting citric acid with a base in the presence of tofacitinib hydrobromide.

The base used to prepare the dihydrogen citrate salt in situ may be an organic base or an inorganic base with a pKa (conjugate acid) higher than that of citric acid. Inorganic bases may be, without limitation, a metal hydroxide, a metal carbonate, a metal bicarbonate, or mixtures thereof. Organic bases may be, without limitation, organic amines including ammonia, primary amines, secondary amines and tertiary amines. For example, suitable bases include, but are not limited to, lithium hydroxide monohydrate, sodium bicarbonate, potassium carbonate, N,N-Diisopropylethylamine, N,N-Diisopropylamine, cesium carbonate, potassium acetate, ammonium acetate, n-butylamine, 1,8-diazabicycloundec-7-ene (DBU), and ammonium hydroxide.

EXAMPLES

The following examples are illustrative of some of the embodiments of the invention described herein. These examples do not limit the spirit or scope of the invention in any way.
Powder X-Ray Diffraction Analysis:

Data were acquired on a PANanalytical X-Pert Pro MPD diffractometer with fixed divergence slits and an X'Celerator RTMS detector. The diffractometer was configured in Bragg-Brentano geometry; data was collected over a 2-theta range of 3 to 40 degrees using CuKα radiation at a power of 40 mA and 45 kV. CuKβ radiation was removed using a divergent beam nickel filter. A step size of 0.017 degrees was used.

Example 1

Preparation of Amorphous Tofacitinib Hydrochloride

A suspension of tofacitinib free base (1.0 g, 3.201 mmol) in isopropanol was heated to 55° C. to dissolve. A solution of approximately 17 wt % hydrogen chloride in isopropanol (825 mg, 3.84 mmol) was added. The solution was then cooled to 23 to 25° C. whereupon slightly gummy solids precipitated out. The suspension was stirred at 23 to 25° C. for 64 hours, filtered and washed with isopropanol (2×12 mL). The damp cake was dried under vacuum (45 torr) at 40° C. (24 hours) to yield amorphous tofacitinib hydrochloride (612 mg).

Example 2

Preparation of Form APO-A Tofacitinib Hydrochloride

A solution of 4M hydrogen chloride in 1,4-dioxane (6.722 mmol) was added to a suspension of tofacitinib free base (2.0 g, 6.402 mmol) in acetone (25 mL). The suspension was stirred at 23 to 25° C. for 16 hours, filtered and washed with acetone (2×10 mL) to yield a damp cake (5.15 g) of tofacitinib hydrochloride as a white solid. A PXRD taken of the damp cake is shown in FIG. 1. A sample was air-dried over 3 days and 2.3 g of this dried material was suspended in refluxing acetone (30 mL) for 24 hours. The suspension was cooled to 23 to 25° C., filtered, washed with acetone (2×5 mL) and air-dried for 16 hours to yield tofacitinib hydrochloride (2.24 g) as a white solid. $^1$H NMR analysis showed a molar ratio of tofacitinib hydrochloride to acetone of approximately 1:0.86 (12.5 wt %). Water content (KF) was 0.0%. A PXRD taken of this sample is shown in FIG. 2.

Example 3

Preparation of Form APO-A Tofacitinib Hydrochloride

A solution of approximately 17 wt % hydrogen chloride in isopropanol (7.684 mmol) was added to a suspension of tofacitinib free base (2.0 g, 6.402 mmol) in acetone (28 mL). The suspension was heated to 45° C. for 4 hours and then cooled to 23 to 25° C. Small amounts of solids were adhered to the walls of the flask which were broken with a spatula. The white suspension was stirred at 23 to 25° C. for 22 hours, filtered, washed with acetone (2×10 mL) and dried under vacuum (5 torr) at 40° C. (3 hours) to yield tofacitinib hydrochloride (2.36 g) as a white solid. $^1$H NMR analysis showed a molar ratio of tofacitinib hydrochloride to acetone of approximately 1:0.82 (12.0 wt %). Water content (KF) was 1.89%. A PXRD taken of the sample is shown in FIG. 3.

Example 4

Preparation of Form APO-B Tofacitinib Hydrochloride

A solution of 4M hydrogen chloride in 1,4-dioxane (g, 2.353 mmol) was added to a suspension of tofacitinib free base (0.7 g, 2.24 mmol) in N,N-dimethylformamide (3 mL). The clear solution was stirred at 23 to 25° C. (3 hours) without any solid formation. Ethyl acetate (2 mL) was added and the resulting turbid solution was stirred at room temperature (16 hours) resulting in the formation of a white suspension. An additional portion (5 mL) of ethyl acetate was added and stirring was continued at 23 to 25° C. for 7 hours. The white suspension was filtered, washed with ethyl acetate (2×5 mL) and air-dried for 16 hours to yield tofacitinib hydrochloride (860 mg). $^1$H NMR analysis showed a molar ratio of tofacitinib hydrochloride to N,N-dimethylformamide of approximately 1:0.8 (14.3 wt %). A PXRD taken of this sample is shown in FIG. 4.

Example 5

Preparation of Form APO-C Tofacitinib Hydrochloride

A solution of 4M hydrogen chloride in 1,4-dioxane (2.353 mmol) was added to a suspension of tofacitinib free base (0.7 g, 2.24 mmol) in dimethyl sulfoxide (3 mL). The clear solution was stirred at 23 to 25° C. (16 hours) without any solid formation. Ethyl acetate (17 mL) was added and the resulting white suspension was heated to 45° C. (2 hours) and cooled to 23 to 25° C. over 4 hours. The white suspension was filtered, washed with ethyl acetate (2×5 mL) and air-dried for 16 hours to yield 830 mg of tofacitinib hydrochloride as a white solid. $^1$H NMR analysis showed a molar ratio of tofacitinib hydrochloride to dimethyl sulfoxide of approximately 1:1 (18.3 wt %). A PXRD taken of this sample is shown in FIG. 5.

Example 6

Preparation of Form APO-D Tofacitinib Hydrochloride

A suspension of amorphous tofacitinib hydrochloride (600 mg) in acetonitrile (5 mL) was heated in a water bath to 45° C.

for 30 minutes and then cooled to 23 to 25° C. The resulting white suspension was stirred at this temperature for 24 hours and filtered, washed with acetonitrile (5 mL) and air-dried for 16 hours to yield 450 mg of tofacitinib hydrochloride as a white solid. $^1$H NMR analysis showed a molar ratio of tofacitinib hydrochloride to acetonitrile of approximately 1:0.05 (0.6 wt %). A PXRD taken of this sample is shown in FIG. 6.

Example 7

Preparation of Form APO-D Tofacitinib Hydrochloride

A solution of 4M hydrogen chloride in 1,4-dioxane (2.353 mmol) was added to a suspension of tofacitinib free base (0.7 g, 2.24 mmol) in acetonitrile (10 mL). A gummy suspension was formed, which was stirred for 26 hours at 23 to 25° C. The resulting white suspension was filtered, washed with acetonitrile (2×5 mL) and air-dried to yield 570 mg of tofacitinib hydrochloride as a white solid. $^1$H NMR analysis showed a molar ratio of tofacitinib hydrochloride to acetonitrile of approximately 1:0.08 (0.9 wt %). A PXRD taken of this sample is shown in FIG. 7. A sample was further dried at 58° C. at 40 torr for 24 hours. $^1$H NMR analysis showed a molar ratio of tofacitinib hydrochloride to acetonitrile of approximately 1:0.01 (0.1 wt %). Water content (KF) was 0.57%. The PXRD remained the same as shown in FIG. 7.

Example 8

Preparation of Form APO-E Tofacitinib Hydrochloride

A solution of 4M hydrogen chloride in 1,4-dioxane (2.353 mmol) was added to a suspension of tofacitinib free base (0.7 g, 2.24 mmol) in N,N-dimethylacetamide (10 mL). The clear solution was stirred at 23 to 25° C. (24 hours) and the resulting white suspension was filtered, washed with ethyl acetate (2×5 mL) and air-dried for 16 hours to yield 655 mg of tofacitinib hydrochloride as a white solid. $^1$H NMR analysis showed a molar ratio of tofacitinib hydrochloride to N,N-dimethylacetamide of approximately 1:0.9 (18.3 wt %). A PXRD taken of this sample is shown in FIG. 8.

Example 9

Preparation of Form APO-F Tofacitinib Hydrochloride

Amorphous tofacitinib hydrochloride (130 mg) was suspended in acetone at 23 to 25° C. over 2 days. The suspension was filtered, washed with acetone (2×1 mL) and dried under vacuum (5 torr) at room temperature (24 h) to yield 102 mg of tofacitinib hydrochloride as a white solid. $^1$H NMR analysis showed a molar ratio of tofacitinib hydrochloride to acetone of approximately 1:0.09 (1.5 wt %). A PXRD taken of this sample is shown in FIG. 9.

Example 10

Preparation of Form APO-G Tofacitinib Hydrochloride

A solution of 4M hydrogen chloride in 1,4-dioxane (2.353 mmol) was added to a suspension of tofacitinib free base (0.7 g, 2.24 mmol) in methyl ethyl ketone (10 mL). The resulting white suspension was stirred for 25 hours at 23 to 25° C., filtered, washed with methyl ethyl ketone (2×5 mL) and air-dried for 16 hours to yield 760 mg of tofacitinib hydrochloride as a white solid. $^1$H NMR analysis showed a molar ratio of tofacitinib hydrochloride to methyl ethyl ketone of approximately 1:0.52 (9.7 wt %). A PXRD taken of this sample is shown in FIG. 10.

Example 11

Preparation of Tofacitinib Citrate

Water (0.4 mL) was added to a sample of the product obtained in Example 2 (1.0 g, 2.508 mmol; containing 12.5 wt % of acetone). Complete dissolution was observed. Water (2.6 mL) and acetone (3 mL) were added followed by solid monosodium citrate (802 mg, 3.44 mmol). After 5 minutes, a white suspension began to form. The suspension was stirred at 23 to 25° C. for 16 hours and the resulting thick, white suspension was filtered, washed with water (3×10 mL) and acetone (5 mL). The damp cake was dried under vacuum (45 torr) at 23 to 25° C. for 24 hours to yield tofacitinib citrate (1.15 g; 91%).

Example 12

Preparation of Tofacitinib Citrate

Water (100 mg) was added to a sample of the product of Example 10 (200 mg, 0.51 mmol; 9.7 wt % of methyl ethyl ketone). Complete dissolution was observed. Water (2 mL) and methyl ethyl ketone (2 mL) were added, followed by solid monosodium citrate (162 mg, 0.688 mmol). After 5 minutes, a white suspension began to form. The suspension was stirred at 23 to 25° C. for 16 hours and the resulting thick, white suspension was filtered, washed with water (2×5 mL) and acetone (3 mL). The damp cake was dried under vacuum (45 torr) at 23 to 25° C. for 24 hours to yield tofacitinib citrate (188 mg; 72%).

Example 13

Preparation of Tofacitinib Citrate

Water (85 mg) was added to a sample of the product of Example 8 (190 mg, 0.444 mmol; containing 18.3 wt % of N,N-dimethylacetamide). Complete dissolution was observed. Water (2 mL) and N,N-dimethylacetamide (1 mL) were added, followed by solid monosodium citrate (155 mg, 0.654 mmol). After 5 minutes, a white suspension began to form. The suspension was stirred at 23 to 25° C. for 16 hours and the resulting thick, white suspension was filtered and washed with water (2×5 mL). The damp cake was dried under vacuum (45 torr) at 23 to 25° C. for 24 hours to yield tofacitinib citrate (210 mg; 94%).

Example 14

Preparation of Tofacitinib Citrate

Water (170 mg) was added to a sample of the product of Example 5 (380 mg, 0.889 mmol; containing 18.3 wt % of dimethyl sulfoxide). Complete dissolution was observed. Water (2 mL) and dimethyl sulfoxide (1 mL) were added, followed by solid monosodium citrate (310 mg, 1.31 mmol). After 5 minutes, a white suspension began to form. The suspension was stirred at 23 to 25° C. for 16 hours and the resulting thick, white suspension was filtered and washed with water (2×5 mL). The damp cake was dried under vacuum (45 torr) at 23 to 25° C. for 24 hours to yield tofacitinib citrate (410 mg; 92%).

Example 15

Preparation of Tofacitinib Citrate

Water (170 mg) was added to a sample of the product of Example 4 (390 mg, 0.957 mmol; containing 14.35 wt % of N,N-dimethyformamide). Complete dissolution was observed. Water (2 mL) and N,N-dimethyformamide (1 mL) were added, followed by solid monosodium citrate (315 mg, 1.34 mmol). After 5 minutes, a white suspension began to form. The suspension was stirred at 23 to 25° C. for 16 hours and the resulting thick, white suspension was filtered and washed with water (2×5 mL). The damp cake was dried under vacuum (45 torr) at 23 to 25° C. for 24 hours to yield tofacitinib citrate (438 mg; 91%).

Example 16

Preparation of Tofacitinib Citrate

Water (70 mg) was added to a sample prepared according to the procedure of Example 7 (150 mg, 0.43 mmol; containing 0.7 wt % of acetonitrile). Complete dissolution was observed. Water (2 mL) and acetonitrile (2 mL) were added, followed by solid monosodium citrate (122 mg, 0.516 mmol). After 5 minutes, a white suspension began to form. The suspension was stirred at 23 to 25° C. for 16 hours and the resulting thick, white suspension was filtered and washed with water (2×3 mL). The damp cake was dried under vacuum (45 torr) at 23 to 25° C. for 24 hours to yield tofacitinib citrate (210 mg; 97%).

Example 17

Preparation of Tofacitinib Citrate

Water (0.5 mL) was added to amorphous tofacitinib hydrochloride (650 mg, 1.863 mmol). Complete dissolution was observed. A solution of citric acid monohydrate (590 mg, 2.795 mmol) and lithium hydroxide monohydrate (95 mg, 2.236 mmol) in water (10 mL) was added. A white suspension was formed in approximately 1 to 2 minutes. The suspension was stirred at 23 to 25° C. for 12 hours, filtered, washed with water (2×10 mL) and acetone (5 mL). The damp cake was dried under vacuum (5 torr) at 23 to 25° C. for 4 hours to yield tofacitinib citrate (820 mg; 87%).

Example 18

Preparation of Tofacitinib Citrate

Water (0.5 mL) was added to amorphous tofacitinib hydrochloride (600 mg, 1.719 mmol). Complete dissolution was observed. A solution of citric acid monohydrate (542 mg, 2.579 mmol) and sodium bicarbonate (175 mg, 2.063 mmol) in water (10 mL) was added. A white suspension was formed in approximately 1 to 2 minutes. The suspension was stirred at 23 to 25° C. for 12 hours, filtered, washed with water (2×10 mL) and acetone (5 mL). The damp cake was dried under vacuum (5 torr) at 23 to 25° C. for 4 hours to yield tofacitinib citrate (700 mg; 81%).

Example 19

Preparation of Tofacitinib Citrate

Water (0.5 mL) was added to amorphous tofacitinib hydrochloride (530 mg, 1.519 mmol). Complete dissolution was observed. A solution of citric acid monohydrate (480 mg, 2.279 mmol) and potassium carbonate (126 mg, 0.911 mmol) in water (10 mL) was added. A white suspension was formed in approximately 1 to 2 minutes. The suspension was stirred at 23 to 25° C. for 12 hours, filtered, washed with water (2×10 mL) and acetone (5 mL). The damp cake was dried under vacuum (5 torr) at 23 to 25° C. for 4 hours to yield tofacitinib citrate (680 mg; 89%).

Example 20

Preparation of Tofacitinib Citrate

Water (0.5 mL) was added to amorphous tofacitinib hydrochloride (600 mg, 1.719 mmol). Complete dissolution was observed. A solution of citric acid monohydrate (542 mg, 2.579 mmol) and N,N-Diisopropylethylamine (270 mg, 2.063 mmol) in water (10 mL) was added. A white suspension was formed in approximately 1 to 2 minutes. The suspension was stirred at 23 to 25° C. for 12 hours, filtered, washed with water (2×10 mL) and acetone (5 mL). The damp cake was dried under vacuum (5 torr) at 23 to 25° C. for 4 hours to yield tofacitinib citrate (690 mg; 80%).

Example 21

Preparation of Tofacitinib Free Base

Crystalline tofacitinib free base was prepared in accordance with the procedure given in Price, Kristin E. et al. *Organic Letters* 2009, 11(9), 2003-2006. The crystalline free base thus obtained was mixed with acetonitrile (25 volumes) and distilled under reduced pressure at 65° C. to approximately 5 volumes. This procedure was repeated twice more. The residue was further dried under vacuum (40 torr) at 45° C. (24 hours) to yield a fluffy solid which showed no substantial impurities by $^1$H NMR. This solid was used throughout the examples described herein.

Example 22

Solubility of Tofacitinib Hydrochloride Solid Forms in Water

Solubility was determined by measuring the quantity of deionized water required to achieve visual dissolution of the solid. The water was added drop-wise to the solid with agitation. With tofacitinib hydrochloride salts, a viscous liquid was obtained.

TABLE A

Comparison of the Solubility of Forms of Tofacitinib Hydrochloride and Tofacitinib Hydrobromide with Crystalline Tofacitinib Citrate.

| Compound | Mass (g) | Amount of deionized water required to obtain complete dissolution | Solubility |
| --- | --- | --- | --- |
| Tofacitinib citrate (crystalline salt as reported in WO 03/048162 A1) | 0.50 | 250 mL | ~2 mg/mL |

TABLE A-continued

Comparison of the Solubility of Forms of Tofacitinib Hydrochloride and Tofacitinib Hydrobromide with Crystalline Tofacitinib Citrate.

| Compound | Mass (g) | Amount of deionized water required to obtain complete dissolution | Solubility |
| --- | --- | --- | --- |
| Tofacitinib hydrochloride (APO-A) | 0.50 | 0.2 g | 2500 mg/mL |
| Tofacitinib hydrochloride (APO-B) | 0.39 | 0.17 g | 2294 mg/mL |
| Tofacitinib hydrochloride (APO-C) | 0.38 | 0.17 g | 2235 mg/mL |
| Tofacitinib hydrochloride (APO-D) | 0.15 | 0.070 g | 2145 mg/mL |
| Tofacitinib hydrochloride (APO-E) | 0.19 | 0.085 g | 2235 mg/mL |
| Tofacitinib hydrochloride (APO-G) | 0.20 | 0.1 g | 2000 mg/mL |
| Tofacitinib hydrobromide (APO-L) | 1.06 | 0.290 g | 3650 mg/mL |

All of the forms of tofacitinib hydrochloride and tofacitinib hydrobromide shown in Table A showed a higher solubility in distilled water compared to the crystalline tofacitinib citrate reported in WO 03/048162 A1.

Example 23

Stability of Form APO-D Tofacitinib Hydrochloride

The polymorphic stability of Form APO-D was assessed as shown in Table B.

TABLE B

Polymorphic Stability of Form APO-D Tofacitinib Hydrochloride

| Sample | Condition | Result |
| --- | --- | --- |
| Form APO-D sample covered by Kimwipe ™ | Fifteen days in ambient conditions | Form APO-D |
| Form APO-D sample covered by Kimwipe ™ with six small punctures | Five hours in 27° C./60% relative humidity chamber | Form APO-D |
| Form APO-D sample covered by Kimwipe ™ with six small punctures | Seventeen hours in 27° C./60% relative humidity chamber | Form APO-D |

Example 24

Preparation of Form APO-A Tofacitinib Hydrochloride

A solution of 4M hydrogen chloride in 1,4-dioxane (3.8 mL, 15.20 mmol) was added to a solution of tofacitinib free base (4.18 g, 13.38 mmol) in acetone (40 mL). The resulting suspension was stirred at 23 to 25° C. for 6 hours, filtered and washed with acetone (2×5 mL) to yield, after air-drying, tofacitinib hydrochloride as a white solid (5.15 g). $^1$H NMR analysis showed a molar ratio of tofacitinib hydrochloride to acetone of approximately 1:0.88 (12.8 wt %). Water content (KF) was 0.69%.

Example 25

Preparation of Form APO-H Tofacitinib Hydrochloride

A solution of 4M hydrogen chloride in 1,4-dioxane (0.6 mL, 2.353 mmol) was added to a solution of tofacitinib free base (0.7 g, 2.24 mmol) in nitromethane (6 mL). Gummy solids were obtained when ethyl acetate (6 mL) was added. Stirring was continued at 23 to 25° C. for 23 hours and the resulting white suspension was filtered, washed with ethyl acetate (2×5 mL) and air-dried to yield 800 mg of tofacitinib hydrochloride as a white solid. $^1$H NMR analysis showed a molar ratio of tofacitinib hydrochloride to nitromethane of approximately 1:0.009 (0.1 wt %). A PXRD taken of this sample is shown in FIG. 11.

Example 26

Preparation of Tofacitinib Hydrochloride

Figure 12:
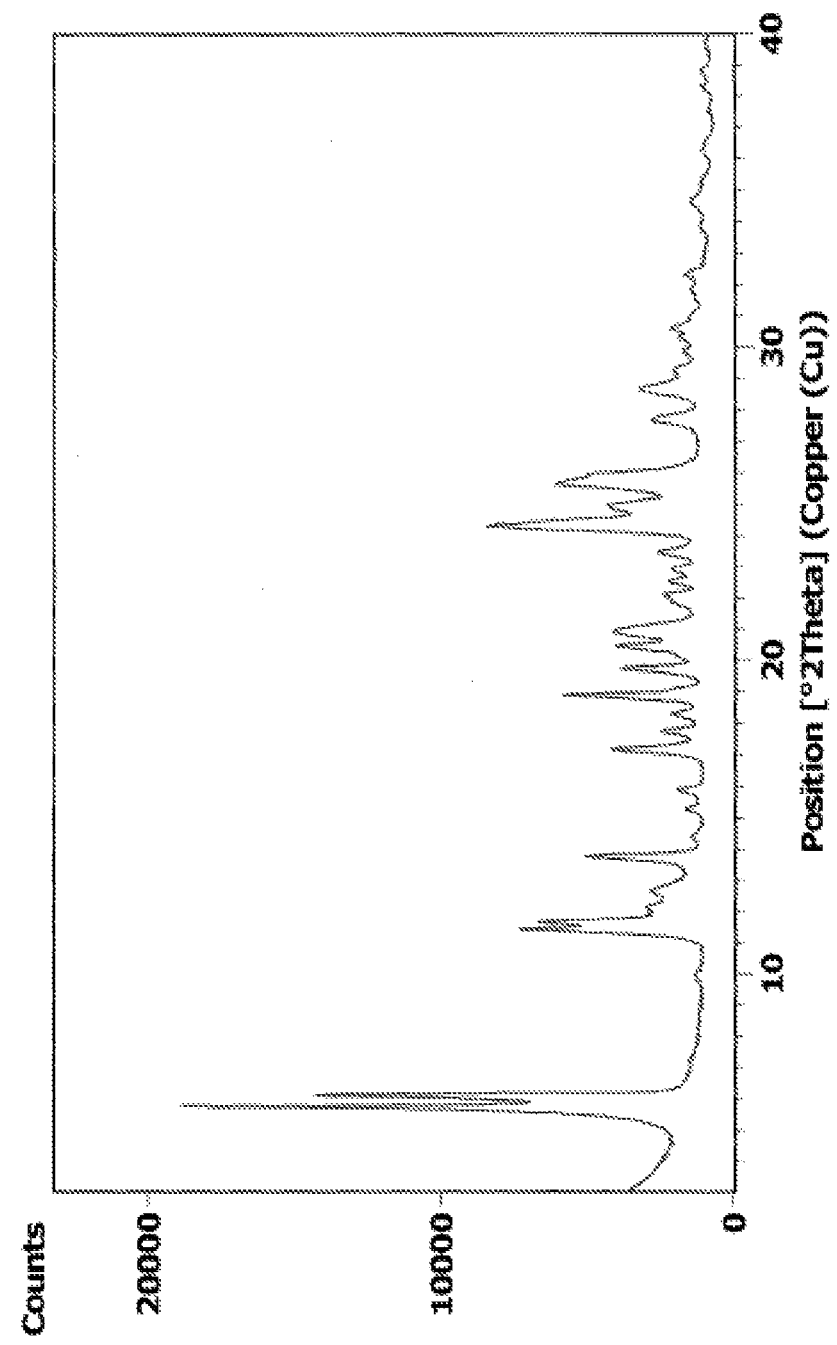
FIG. 12 is a Powder X-Ray Diffractogram (PXRD) of tofacitinib hydrochloride obtained according to Example 26.

A solution of 37% aqueous hydrogen chloride (240 mg, 2.36 mmol) was added to a solution of tofacitinib free base (0.7 g, 2.24 mmol) in acetone (10 mL). Stirring was continued at 23 to 25° C. for 23 hours and the resulting white suspension was filtered, washed with acetone (2×5 mL) and air-dried to yield 820 mg of tofacitinib hydrochloride as a white solid. $^1$H NMR analysis showed a molar ratio of tofacitinib hydrochloride to acetone of approximately 1:0.13 (2.1 wt %). A PXRD taken of this sample is shown in FIG. 12.

Example 27

Preparation of Tofacitinib Citrate

Water (1 mL) was added to a sample of the product obtained in Example 24 (1.01 g, 2.51 mmol; containing 12.8 wt % of acetone and 0.69% water). Complete dissolution was observed. A solution of citric acid monohydrate (0.64 g, 3.07 mmol) and cesium carbonate (1.02 g, 3.13 mmol) in water (10 mL) was added. A suspension was formed in approximately 1 to 2 minutes. The suspension was then treated with 4M hydrogen chloride in 1,4-dioxane (2.60 mmol). The resulting white suspension (pH=3) was stirred at 23 to 25° C. for 16 hours, filtered and washed with water (2×5 mL). The damp cake was dried under vacuum (34 torr) at 40 to 45° C. for 56 hours to yield tofacitinib citrate (1.09 g; 86%).

Example 28

Preparation of Tofacitinib Citrate

Water (1 mL) was added to a sample of the product obtained in Example 24 (1.01 g, 2.51 mmol; containing 12.8 wt % of acetone and 0.69% water). Complete dissolution was observed. A suspension of magnesium citrate pentahydrate (0.93 g, 3.06 mmol) in water (20 mL) was added. The suspension was then treated with 4M hydrogen chloride in 1,4-dioxane (2.80 mmol), the resulting suspension was stirred at 23 to 25° C. for 16 hours, filtered and washed with water (2×5 mL). The damp cake was dried under vacuum (34 Ttorr) at 40 to 45° C. for 56 hours to yield tofacitinib citrate (1.17 g; 92%).

Example 29

Preparation of Tofacitinib Citrate

Water (1 mL) was added to a sample of the product obtained in Example 24 (1.01 g, 2.51 mmol; containing 12.8 wt % of acetone and 0.69% water). Complete dissolution was observed. A solution of citric acid monohydrate (0.65 g, 3.10 mmol) and potassium acetate (0.28 g, 2.84 mmol) in water (10 mL) was added. A suspension was formed in approximately 5 minutes. The resulting white suspension was stirred at 23 to 25° C. for 16 hours, filtered and washed with water (2×5 mL). The damp cake was dried under vacuum (34 torr) at 40 to 45° C. for 16 hours to yield tofacitinib citrate (1.18 g; 93%).

Example 30

Preparation of Tofacitinib Citrate

Water (1 mL) was added to a sample of the product obtained in Example 24 (1.06 g, 2.62 mmol; containing 12.8 wt % of acetone and 0.69% water). Complete dissolution was observed. A solution of citric acid monohydrate (0.67 g, 3.21 mmol) and ammonium acetate (0.25 g, 3.22 mmol) in water (10 mL) was added. A suspension was formed in approximately 5 minutes. The resulting white suspension was stirred at 23 to 25° C. for 16 hours, filtered and washed with water (2×5 mL). The damp cake was dried under vacuum (34 torr) at 40 to 45° C. for 16 hours to yield tofacitinib citrate (1.25 g; 94%).

Example 31

Preparation of Tofacitinib Citrate

Form APO-A tofacitinib hydrochloride (0.80 g, 2.29 mmol) was dissolved in water (0.80 mL). A solution of citric acid (0.53 g, 2.75 mmol) and N,N-diisopropylamine (0.25 g, 2.52 mmol) in water (8 mL) was charged under stirring at room temperature. Solids started to form 1-2 minutes following addition. The suspension was stirred at room temperature for 4 hours then filtered and washed with water (2×5 mL) and acetone (1×3 mL). The filtered solids were dried under vacuum (35 torr) at 40° C. for approximately 5 hours to yield tofacitinib citrate (1.06 g; 92%) as a white solid.

Example 32

Preparation of Tofacitinib Citrate

Form APO-A tofacitinib hydrochloride (0.80 g, 2.29 mmol) was dissolved in water (0.80 mL). A solution of citric acid (0.53 g, 2.75 mmol) and n-butylamine (0.18 g, 2.52 mmol) in water (8 mL) was charged under stirring at room temperature. Solids started to form 1-2 minutes following addition. The suspension was stirred at room temperature for 4 hours then filtered and washed with water (2×5 mL) and acetone (1×3 mL). The filtered solids were dried under vacuum (35 torr) at 40° C. for approximately 5 hours to yield tofacitinib citrate (1.04 g; 90%) as a white solid.

Example 33

Preparation of Tofacitinib Citrate

Form APO-A tofacitinib hydrochloride (0.80 g, 2.29 mmol) was dissolved in water (0.80 mL). A solution of citric acid (0.53 g, 2.75 mmol) and 1,8-diazabicycloundec-7-ene (DBU) (0.38 g, 2.52 mmol) in water (8 mL) was charged under stirring at room temperature. Solids started to form 1-2 minutes following addition. The suspension was stirred at room temperature for 4 hours then filtered and washed with water (2×5 mL) and acetone (1×3 mL). The filtered solids were dried under vacuum (35 torr) at 40° C. for approximately 5 hours to yield tofacitinib citrate (1.03 g; 89%) as a white solid.

Example 34

Preparation of Tofacitinib Citrate

Form APO-A tofacitinib hydrochloride (0.80 g, 2.29 mmol) was dissolved in water (0.80 mL). A solution of citric acid (0.53 g, 2.75 mmol) and aqueous ammonium hydroxide (28 wt %, 0.15 g, 2.52 mmol) in water (8 mL) was charged under stirring at room temperature. Solids started to form 1-2 minutes following addition. The suspension was stirred at room temperature for 4 hours then filtered and washed with water (2×5 mL) and acetone (1×3 mL). The filtered solids were dried under vacuum (35 torr) at 40° C. for approximately 5 hours to yield 1.04 g of tofacitinib citrate (1.04 g; 90%) as a white solid.

Example 35

Preparation of Tofacitinib Citrate

Form APO-A tofacitinib hydrochloride (0.50 g, 1.43 mmol) was dissolved in water (0.50 mL). A solution of citric acid (0.33 g, 1.72 mmol) in water (5 mL) was charged and the mixture was stirred at room temperature. Solids started to form 1-2 minutes following addition. The suspension was stirred at room temperature for approximately 6 hours then filtered and washed with water (2×5 mL) and acetone (1×3 mL). The filtered solids were left to air dry for 16 hours and yielded tofactinib citrate (0.39 g; 54%) as a white solid.

Example 36

Preparation of Amorphous Tofacitinib Hydrobromide

An aqueous solution (48 wt %) of hydrogen bromide (3.44 g, 20.4 mmol) was added to a solution of tofacitinib free base (5.60 g, 17.9 mmol) in acetone (30 mL). The resulting oily suspension was stirred for 1 hour at 25° C. before acetone was removed in vacuo by rotary evaporation and the residual solid was dried under vacuum (8 torr) for 16 hours at 25° C. to yield 7.08 g of amorphous tofacitinib hydrobromide as a pale orange solid. $^1$H NMR analysis showed a residual acetone content of approximately 1.0 wt %.

Example 37

Preparation of Form APO-I Tofacitinib Hydrobromide

Amorphous tofacitinib hydrobromide (0.54 g) was treated with acetonitrile (5.5 mL). The suspension was stirred at 25° C. for 3 days, heated at 40° C. for 1 hour, and then stirred at 25° C. for 16 hours. The resulting off-white suspension was filtered, washed with acetonitrile (2×5 mL) and air-dried for 16 hours at 25° C. to yield 0.23 g of tofacitinib hydrobromide as an off-white solid. $^1$H NMR analysis showed a molar ratio of tofacitinib hydrobromide to acetonitrile of approximately 1:0.51 (5.0 wt %). A PXRD taken of the sample is shown in FIG. 13.

Example 38

Preparation of Form APO-J Tofacitinib Hydrobromide

Amorphous tofacitinib hydrobromide (0.54 g) was treated with acetone (5 mL). The suspension was heated to reflux for 1 hour, cooled down to 25° C., and stirred for 3 days. The resulting off-white suspension was filtered, washed with acetone (2×5 mL) and air-dried for 16 hours at 25° C. to yield 0.19 g of tofacitinib hydrobromide as an off-white solid. $^1$H NMR analysis showed a molar ratio of tofacitinib hydrobromide to acetone of approximately 1:0.43 (6.0 wt %). A PXRD taken of the sample is shown in FIG. 14.

Example 39

Preparation of Form APO-K Tofacitinib Hydrobromide

Amorphous tofacitinib hydrobromide (0.48 g) was treated with a 1:5 mixture of ethyl acetate:N,N-dimethylformamide (5 mL). The suspension was stirred for 3 days, the resulting off-white suspension was filtered, washed with ethyl acetate (2×5 mL), and air-dried for 16 hours at 25° C. to yield 0.17 g of tofacitinib hydrobromide as an off-white solid. $^1$H NMR analysis showed a molar ratio of tofacitinib hydrobromide to N,N-dimethylformamide of approximately 1:0.78 (12.7 wt %). A PXRD taken of this sample is shown in FIG. 15.

Example 40

Preparation of Form APO-L Tofacitinib Hydrobromide

Amorphous tofacitinib hydrobromide (0.51 g) was treated with a 1:5 mixture of ethyl acetate:N,N-dimethylacetamide (6 mL). The suspension was stirred for 3 days, the resulting off-white suspension was filtered, washed with ethyl acetate (2×5 mL) and air-dried for 16 hours at 25° C. to yield 0.22 g of tofacitinib hydrobromide as an off-white solid. $^1$H NMR analysis showed a molar ratio of tofacitinib hydrobromide to N,N-dimethylacetamide of approximately 1:0.81 (15.2 wt %). A PXRD taken of this sample is shown in FIG. 16.

Example 41

Preparation of Form APO-M Tofacitinib Hydrobromide

Amorphous tofacitinib free base (0.70 g, 2.24 mmol) was dissolved in acetone (10 mL). To the clear solution was charged aqueous hydrogen bromide (48%, 0.38 g, 2.24 mmol) in one portion at 23 to 25° C. Initially, a white suspension formed which then quickly aggregated to a very thick oil. After stirring for 3 days, a white solid had formed on the walls of the flask. The white solid was scraped into the liquid and further stirred at room temperature for an additional 16 hours. The white suspension was filtered and washed with acetone (2×5 mL) and dried under vacuum (35 torr) for 16 hours at 23 to 25° C. to yield 0.67 g of solid tofacitinib hydrobromide. $^1$H NMR analysis showed a molar ratio of tofacitinib hydrobromide to acetone of approximately 1:0.39 (5.4 wt %) Water content (KF) was 0.88%. A PXRD taken of this sample is shown in FIG. 17.

Example 42

Preparation of Form APO-N Tofacitinib Hydrobromide

Amorphous tofacitinib free base (0.70 g, 2.24 mmol) was dissolved in acetone (3 mL). To the clear solution was charged a solution of hydrogen bromide (7.2 mL) in acetone (0.314 M, prepared by addition of 1.93 g of acetyl bromide and 0.50 g of methanol to 50 mL of acetone, 2.26 mmol) in one portion and the white suspension was stirred at 23 to 25° C. for 16 hours. The white suspension was filtered, washed with acetone (2×10 mL) and dried under vacuum (35 torr) for 16 hours to yield 0.55 g of tofacitinib hydrobromide as a white solid. $^1$H NMR analysis showed a molar ratio of tofacitinib hydrobromide to acetone of approximately 1:0.7 (9.4 wt %) Water content (KF) was 0.88%. A PXRD taken of this sample is shown in FIG. 18.

Example 43

Preparation of Tofacitinib Citrate

A sample of the product obtained in Example 37 (0.09 g) was dissolved in water (2 mL). The solution was treated with solid monosodium citrate (64.5 mg, 0.23 mmol) and the resulting white suspension was stirred for 16 hours at 25° C. The suspension was filtered, washed with water (2×5 mL) and air-dried for 16 hours at 25° C. to yield 0.06 g of tofacitinib citrate as a white solid.

Example 44

Preparation of Tofacitinib Citrate

A sample of the product obtained in Example 39 (74.3 mg) was dissolved in water (2 mL). The solution was treated with solid monosodium citrate (54.3 mg, 0.23 mmol) and the resulting white suspension was stirred for 16 hours at 25° C. The suspension was filtered, washed with water (2×2 mL) and air-dried for 16 hours at 25° C. to yield 51.6 mg of tofacitinib citrate as a white solid.

Example 45

Preparation of Tofacitinib Citrate

A sample of the product obtained in Example 40 (170.1 mg) was dissolved in water (4 mL). The solution was treated with solid monosodium citrate (121.1 mg, 0.52 mmol) and the resulting white suspension was stirred for 16 hours at 25° C. The suspension was filtered, washed with water (2×3 mL) and air-dried for 16 hours at 25° C. to yield 145.0 mg of tofacitinib citrate as a white solid.

Example 46

Preparation of Tofacitinib Citrate

Amorphous tofacitinib hydrobromide (0.55 g) was dissolved in water (6 mL). The solution was treated with solid monosodium citrate (0.40 g, 1.69 mmol) and the resulting white suspension was stirred for 16 hours at 25° C. The suspension was filtered, washed with water (2×5 mL) and air-dried for 16 hours at 25° C. to yield 0.63 g of tofacitinib citrate as a white solid.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range. The word "comprising" is used herein as an open-ended term, substantially equivalent to the phrase "including, but not limited to", and the word "comprises" has a corresponding meaning. As used herein, the singular forms "a", "an" and "the" include plural references unless the context clearly dictates otherwise. Thus, for example, reference to "a thing" includes more than one such thing. Citation of references herein is not an admission that such references are prior art to the present invention. Furthermore, material appearing in the background section of the specification is not an admission that such material is prior art to the invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A process for the preparation of tofacitinib citrate, the process comprising combining at least one of:
   i) tofacitinib hydrochloride; or
   ii) tofacitinib hydrobromide,
with a source of citrate ion.

2. The process of claim 1 wherein the source of citrate ion is citric acid or a dihydrogen citrate salt.

3. The process of claim 2 wherein the dihydrogen citrate salt is an alkali metal dihydrogen citrate salt or monosodium citrate.

4. The process of claim 3 wherein the dihydrogen citrate salt is prepared in situ by reacting, in the presence of tofacitinib hydrochloride or tofacitinib hydrobromide, citric acid with a base selected from the group consisting of metal hydroxides, metal carbonates, metal bicarbonates and amines.

* * * * *